US011267891B2

(12) United States Patent
Blein et al.

(10) Patent No.: US 11,267,891 B2
(45) Date of Patent: Mar. 8, 2022

(54) FC VARIANT ANTIBODIES AND THEIR USES

(71) Applicant: Sanofi, Paris (FR)

(72) Inventors: Stanislas Blein, Cernier (CH); Samuel Hou, Neuchatel (CH); Darko Skegro, Grenchen (CH)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/607,345

(22) Filed: Jan. 28, 2015

(65) Prior Publication Data

US 2015/0232559 A1   Aug. 20, 2015

Related U.S. Application Data

(63) Continuation of application No. 13/578,921, filed as application No. PCT/IB2011/000344 on Feb. 22, 2011, now Pat. No. 8,975,376.

(60) Provisional application No. 61/307,009, filed on Feb. 23, 2010.

(51) Int. Cl.
C07K 16/00 (2006.01)
C07K 16/46 (2006.01)
C07K 16/28 (2006.01)

(52) U.S. Cl.
CPC ...... *C07K 16/2839* (2013.01); *C07K 16/2842* (2013.01); *C07K 2317/24* (2013.01); *C07K 2317/52* (2013.01); *C07K 2317/524* (2013.01); *C07K 2317/72* (2013.01); *C07K 2317/732* (2013.01); *C07K 2317/734* (2013.01); *C07K 2317/76* (2013.01)

(58) Field of Classification Search
None
See application file for complete search history.

(56) References Cited

U.S. PATENT DOCUMENTS

| 6,737,056 | B1 | 5/2004 | Presta |
| 7,700,321 | B2 | 4/2010 | McPherson et al. |
| 2004/0228856 | A1 | 9/2004 | Presta |
| 2007/0009523 | A1 | 1/2007 | Presta |
| 2007/0128190 | A1 | 6/2007 | Lazarides et al. |
| 2007/0141052 | A1 | 6/2007 | Watkins et al. |
| 2008/0138349 | A1 | 6/2008 | Stavenhagen et al. |
| 2008/0242845 | A1 | 10/2008 | Lazar et al. |
| 2009/0004186 | A1 | 1/2009 | Shitara et al. |
| 2010/0047243 | A1 | 2/2010 | Burden et al. |
| 2010/0215651 | A1 | 2/2010 | Blein et al. |
| 2011/0059075 | A1 | 3/2011 | Wittrup et al. |
| 2012/0100140 | A1 | 4/2012 | Reyes et al. |

FOREIGN PATENT DOCUMENTS

| CA | 2676529 | A1 | 7/2008 |
| CN | 101360826 | A | 2/2009 |
| EA | 7617 | B1 | 8/2001 |
| JP | 2009516506 | A | 4/2009 |
| JP | 2012518404 | A | 8/2012 |
| JP | 59-72176 | B2 | 8/2016 |
| JP | 62-76310 | B2 | 2/2018 |
| KR | 10-2006-0067983 | A | 6/2006 |
| KR | 1020080074184 | A | 8/2008 |
| KR | 1020090114449 | A | 11/2009 |
| WO | 2000042072 | A2 | 7/2000 |
| WO | 2004/056308 | A2 | 7/2004 |
| WO | 2006/023420 | A2 | 3/2006 |
| WO | 2006/053301 | A2 | 5/2006 |
| WO | 2006/089133 | A2 | 8/2006 |
| WO | 2006105338 | A2 | 10/2006 |
| WO | 2007041635 | A2 | 4/2007 |
| WO | 2007044616 | A2 | 4/2007 |
| WO | 2007056858 | A1 | 5/2007 |
| WO | 2007/106707 | A2 | 9/2007 |
| WO | 2008090959 | A1 | 7/2008 |
| WO | 2008114011 | A2 | 9/2008 |
| WO | 2008156622 | A1 | 12/2008 |
| WO | WO2009079242 | * | 6/2009 |
| WO | 2010095031 | A2 | 11/2010 |
| WO | 2011005481 | A1 | 1/2011 |
| WO | 2011091078 | A2 | 7/2011 |

OTHER PUBLICATIONS

Hughes et al. Platelet integrin α2 I-domain specific antibodies produced via domain specific DNA vaccination combined with variable gene phage display Thromb Haemost 2005; 94: 1318-26. (Year: 2005).*
Jefferies et al. (1998) "IgG-Fc-mediated effector functions: molecular definition of interaction sites for effector ligands and the role of glycosylation," Immunological Reviews. 163:59-76.
Moore et al. (Mar. 2010) "Engineered Fc variant antibodies with enhanced ability to recruit complement and mediate effector functions," mAbs. 2:181-189.
Nose et al. (1989) "Substitution of asparagine324 with aspartic acid in the Fc portion of mouse antibodies reduces their capacity for C1q binding," European Journal of Immunology. 19:2179-2181.
Office Action corresponding to Chinese Patent Application No. 201180020557.6, dated Nov. 25, 2013—with English translation.
Office Action corresponding to Korean Patent Application No. 10-2012-7024656, dated Mar. 19, 2015—with English translation.
Extended European Search Report with Written Opinion corresponding to European Patent Application No. 14197411.3, dated Feb. 2, 2015.

(Continued)

*Primary Examiner* — Maher M Haddad
(74) *Attorney, Agent, or Firm* — Lathrop Gpm LLP; James H. Velema; Judith L. Stone-Hulslander

(57) ABSTRACT

The invention relates to antibodies directed to α2β1 integrin and their uses, including humanized anti-alpha 2 (α2) integrin antibodies and methods of treatment with anti-α2 integrin antibodies. More specifically the present invention relates to humanized anti-α2 integrin antibodies comprising a heavy chain variable region, a light chain variable region, a human light chain constant region and a variant human IgG1 heavy chain constant region which exhibit altered effector function.

10 Claims, 3 Drawing Sheets

Specification includes a Sequence Listing.

(56) References Cited

OTHER PUBLICATIONS

Notification of Reasons for Refusal corresponding to Japanese Patent Application No. 2012-554433, dated Mar. 24, 2015—with English translation.
Argraves (1987) "Amino Acid Sequence of the Human Fibronectin Receptor," J. Cell. Biol. Sep. 105(3):1183-90.
Bhatt et al. (2003) "Scientific and Therapeutic Advances in Antiplatelet Therapy", Nat. Rev. Drug Discov., 2(1):15-28.
Brown et al. (1996) "Tolerance of single, but not multiple, amino acid replacements in antibody VH CDR 2: a means of minimizing B cell wastage from somatic hypermutation?." The Journal of Immunology. 156(9):3285-3291.
De Fougerolles et al. (2000) "Regulation of inflammation by collagen-binding integrins a1b1 and a2b1 in models of hypersensitivity and arthritis," J. Clin. Invest. 105:721-729.
Emsley et al. (1997) "Crystal Structure of the I Domain from Integrin a2b1," J. Biol. Chem. 272(45):28512-28517.
Hangan et al. (1996) "Integrin VLA-2 (a2b1) Function in Postextravasation Movement of Human Rhabdomyosarcoma RD Cells in the Liver," Cancer Res. 56:3142-3149.
Idusogie et al. (2000) "Mapping of the C1q Binding Site on Rituxan, a Chimeric Antibody with a Human IgG1 Fc," J. Immunol. Methods. 164:4178-4184.
International Search Report and Written Opinion in related application PCT/IB11/00344, 8 pages.
Kamata et al. (1994) "Identification of Putative Ligand Binding Sites within I Domain of Integrin a2bI (VLA-2, CD49b/CD29)," J. Biol. Chem. 269(13):9659-9663.
Kriegelstein et al. (2002) "Collagen-binding integrin a1b1 regulates intestinal inflammation in experimental colitis," J. Clininvest. 110(12):1773-1782.
Natsume et al. (2008) "Engineered antibodies of the IgG1/IgG3 mixed isotype with enhanced cytotoxic activities," Cancer Research. 68(10):3863-3872.
Nieswandt et al. (2003) "Platelet-collagen interaction: is GPVI the central receptor?," Blood. 102(2):449-461.
Sazinsky (2008) "Engineering aglycosylated antibody variants with immune effector functions," Massachusetts Institute of Technology. Dept. of Biological Engineering. Dissertation, pp. 1-114.
Schumaker et al. (1976) "Ultracentrifuge Studies of the Binding of IgG of Different Subclasses to the C1q Subunit of the First Component of Complement," Biochemistry. 15:5175-5181.
Senger et al. (2002) "The a1b1 and a2b1 Integrins Provide Critical Support for Vascular Endothelial Growth Factor Signaling, Endothelial Cell Migration, and Tumor Angiogenesis," Am. J. Pathol. 160(1):195-204.
Takada et al. (1989) "The Primary Structure of the VLA-2/Collagen Receptor a2 Subunit (Platelet GPIa): Homology to Other Integrins and the Presence of a Possible Collagen-binding Domain," J. Cell Biol. 109:397-407.
Umana et al. (2006) "Novel 3(rd) generation humanized type IICD20 antibody with glycoengineered fc and modified elbow hinge for enhanced ADCC and superior apoptosis induction," Blood. Vol. 108. No. 11. Part 1. p. 72A. (Abstract of Oral Sessions).
Vanhoorelbeke et al. (2003) "Inhibition of Platelet Adhesion to Collagen as a New Target for Antithrombotic Drugs," Curr. Drug Targets Cardiovasc. Haematol. Disord. 3(2):125-40.
Winkler et al. (2000) "Changing the antigen binding specificity by single point mutations of an anti-p24 (HIV-1) antibody," The Journal of Immunology. 165(8):4505-4514.
Ohno et al. (1985) "Antigen-binding specificities of antibodies are primarily determined by seven residues of VH," Proc. Natl. Acad. Sci. USA, 82:2945-2949.
Rudikoff et al. (1982) "Single amino acid substitution altering antigen-binding specificity," Proc. Natl. Acad. Sci. USA, 79:1979-1983.
Yarilin A. A., Basics of Immunology, 1999, pp. 354-358.
Yarilin A. A., Basics of Immunulogy, 1999, pp. 172-174.

* cited by examiner

FC VARIANT ANTIBODIES AND THEIR USES

This application is a continuation of U.S. patent application Ser. No. 13/578,921, filed Aug. 14, 2012, now U.S. Pat. No. 8,975,376, which is a 371 National Phase Entry application of International Application PCT/IB2011/000344, filed Feb. 22, 2011, which designated the U.S. and which claims the benefit under 35 U.S.C. § 119 of U.S. Application No. 61/307,009, filed Feb. 23, 2010. The contents of these applications are incorporated herein by reference in their entirety.

TECHNICAL FIELD

The present invention generally relates to antibodies directed to α2β1 integrin and their uses, including humanized anti-alpha 2 (α2) integrin antibodies and methods of treatment with anti-α2 integrin antibodies. More specifically the present invention relates to humanized anti-α2 integrin antibodies comprising a heavy chain variable region, a light chain variable region, a human light chain constant region and a variant human IgG1 heavy chain constant region which exhibit altered effector function.

BACKGROUND OF THE INVENTION

The integrin α2β1 (Very late antigen 2; VLA-2) is expressed on a variety of cell types including platelets, vascular endothelial cells, epithelial cells, activated monocytes/macrophages, fibroblasts, leukocytes, lymphocytes, activated neutrophils and mast cells. (Hemler, Annu Rev Immunol 8:365:365-400 (1999); Wu and Santoro, Dev. Dyn. 206:169-171 (1994); Edelson et. al., Blood. 103(6):2214-20 (2004); Dickeson et al, Cell Adhesion and Communication. 5: 273-281 (1998)). The most typical ligands for α2β1 include collagen and laminin, both of which are found in extracellular matrix. Typically the I-domain of the α2 integrin binds to collagen in a divalent-cation dependent manner whereas the same domain binds to laminin through both divalent-cation dependent and independent mechanisms. (Dickeson et al, Cell Adhesion and Communication. 5: 273-281 (1998)). The specificity of the α2β1 integrin varies with cell type and serves as a collagen and/or laminin receptor for particular cell types, for example α2β1 integrin is known as a collagen receptor for platelets and a laminin receptor for endothelial cells. (Dickeson et al, J Biol. Chem. 272: 7661-7668 (1997)) Echovirus-1, decorin, E-cadherin, matrix metalloproteinase I (MMP-I), endorepellin and multiple collectins and the C1q complement protein are also ligands for α2β1 integrin. (Edelson et al., Blood 107(1): 143-50 (2006)) The α2β1 integrin has been implicated in several biological and pathological processes including collagen-induced platelet aggregation, cell migration on collagen, cell-dependent reorganization of collagen fibers as well as collagen-dependent cellular responses that result in increases in cytokine expression and proliferation, (Gendron, J. Biol. Chem. 278:48633-48643 (2003); Andreasen et al., J. Immunol. 171:2804-2811 (2003); Rao et al., J. Immunol. 165(9):4935-40 (2000)), aspects of T-cell, mast cell, and neutrophil function (Chan et. al., J. Immunol. 147:398-404 (1991); Dustin and de Fougerolles, Curr Opin Immunol 13:286-290 (2001), Edelson et. al., Blood. 103(6): 2214-20 (2004), Werr, et al., Blood 95:1804-1809 (2000), aspects of delayed type hyersensitivity contact hypersensitivity and collagen-induced arthritis (de Fougerolles et. al., J. Clin. Invest. 105:721-720 (2000); Kriegelstein et al., J. Clin. Invest. 110(12):1773-82 (2002)), mammary gland ductal morphogenesis (Keely et. al., J. Cell Sci. 108:595-607 (1995); Zutter et al., Am. J. Pathol. 155(3):927-940 (1995)), epidermal wound healing (Pilcher et. al., J. Biol. Chem. 272:181457-54 (1997)), and processes associated with VEGF-induced angiogenesis (Senger et al., Am. J. Pathol. 160(1):195-204 (2002)).

Integrin/ligand interactions can facilitate leukocyte extravasation into inflamed tissues (Jackson et al., J. Med. Chem. 40:3359-3368 (1997); Gadek et al., Science 295 (5557):1086-9 (2002), Sircar et al., Bioorg. Med. Chem. 10:2051-2066 (2002)), and play a role in downstream events following the initial extravasation of leukocytes from the circulation into tissues in response to inflammatory stimuli, including migration, recruitment and activation of pro-inflammatory cells at the site of inflammation (Eble J. A., Curr. Phar. Des. 11(7):867-880 (2005)). Some antibodies that block α2β1 integrin were reported to show impact on delayed hypersensitivity responses and efficacy in a murine model of rheumatoid arthritis and a model of inflammatory bowel disease (Kriegelstein et al., J. Clin. Invest. 110(12): 1773-82 (2002); de Fougerolles et. al., J. Clin. Invest. 105:721-720 (2000) and were reported to attenuate endothelial cell proliferation and migration in vitro (Senger et al., Am. J. Pathol. 160(1):195-204 (2002), suggesting that the blocking of α2β1 integrin might prevent/inhibit abnormal or higher than normal angiogenesis, as observed in various cancers.

It is anticipated that a therapeutic antibody that binds α2β1 integrin, including the α2β1 integrin on platelets, could result in bleeding complications. For example, antibodies targeting other platelet receptors-such as GPIb (Vanhoorelbeke et al., Curr. Drug Targets Cardiovasc. Haematol. Disord. 3(2):125-40 (2003) or GP IIb/IIIa (Schell et al., Ann. Hematol. 81:76-79 (2002), Nieswandt and Watson, Blood 102(2):449-461 (2003), Merlini et al., Circulation 109:2203-2206 (2004)) have been associated with thrombocytopenia, although the mechanisms behind this are not well understood. It has been hypothesized that binding of an antibody to a platelet receptor can alter its three dimensional structure, and expose normally unexposed epitopes which then leads to platelet elimination (Merlini et al., Circulation 109:2203-2206 (2004). Indeed, the bleeding complications associated with oral doses of GP IIa/IIIb antagonists have been described as the "dark side" of this class of compounds (Bhatt and Topol, Nat. Rev. Drug Discov. 2(1):15-28 (2003)). If α2β1 integrin plays an important role in the movement of leukocytes through inflammatory tissue, it would be desirable to develop therapeutic agents that could target α2β1 for diseases α2β1 integrin-associated disorders and/or cellular processes associated with the disorders, including cancer, inflammatory diseases and autoimmune diseases, if such agents would not activate platelets. Humanized antibodies capable of targeting α2β1 integrin, such as the α2β1 integrin on leukocytes, which are not associated with adverse bleeding complications are described in WO2007/056858. The humanized anti-α2 integrin antibodies described therein represent a novel subgroup of anti-α2 antibodies, which are characterized by an unexpected lack of in vivo bleeding complications and/or by a lack of platelet α2β1 integrin activation. The IgG4 antibodies disclosed in WO2007/056858, however, do not carry effector functions such as ADCC and/or CDC, which are desired under certain circumstances, e.g. for the treatment of α2β1 integrin-associated disorders such as cancer, where this functionality leads to increased efficacy of treatment. Thus, it would be desirable to develop anti-α2β1 integrin antibodies that would exhibit these effector functions to a high degree.

SUMMARY OF THE INVENTION

Figure 1:
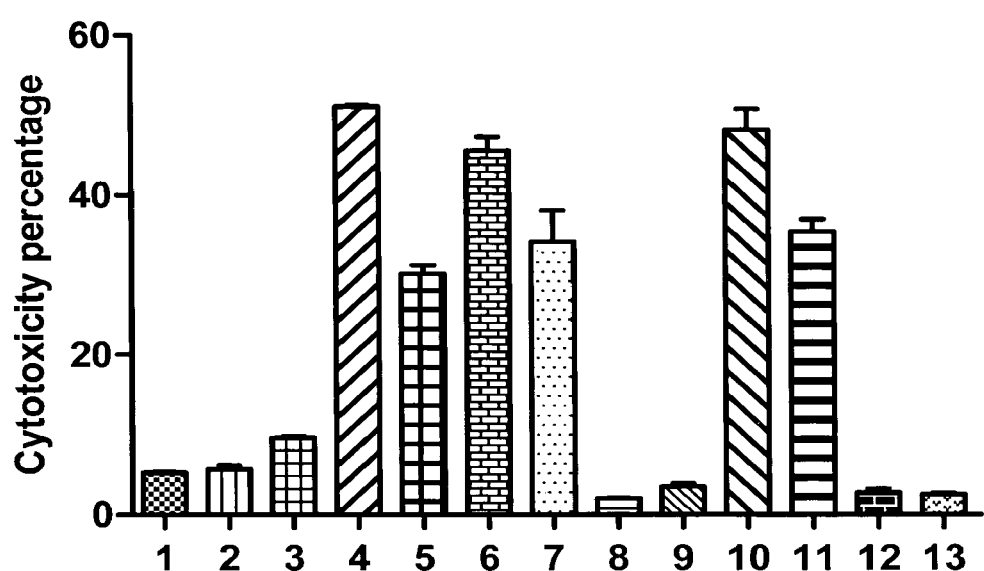
FIG. 1 shows cell-based CDC assay of selected anti-VLA2 antibody variants: (1) anti-VLA2 IgG4; (2) anti-VLA2 IgG1; (3) anti-VLA2 IgG2; (4) anti-VLA2 IgG3; (5) anti-VLA2 IgG1133; (6) anti-VLA2 IgG3133; (7) anti-VLA2 IgG1-S324N; (8) anti-VLA2 IgG1-S298A, (9) anti-VLA2 IgG1-E269D; (10) anti-VLA2 IgG1-E269D/S298A/S324N; (11) anti-VLA2 IgG1-S298A/S324N; (12) IgG1 control; (13) negative control—no antibody.

The present invention provides a humanized anti-α2 integrin antibody comprising a heavy chain variable region, a light chain variable region, a human light chain constant region and a variant human IgG1 heavy constant domain, whereas the variant human IgG1 heavy chain constant region comprises at least one amino acid modification relative to the human IgG1 heavy chain constant region of the parent humanized anti-α2 integrin antibody, and whereas the antibody exhibits altered effector function compared to the parent humanized anti-α2 integrin antibody.

The invention further provides an isolated nucleic acid encoding the above-mentioned humanized anti-α2β1 integrin antibody.

The invention further provides a vector comprising the above-mentioned nucleic acid.

The invention further provides a host cell comprising the above-mentioned nucleic acid or the above-mentioned vector.

The invention further provides a composition comprising the above-mentioned humanized anti-α2 integrin antibody and a pharmaceutically acceptable carrier.

The invention further provides a kit comprising the above-mentioned humanized anti-α2 integrin or the above-mentioned composition and instructions for the treatment of an α2β1 integrin-associated disorder.

The invention further provides a method of treating an α2β1 integrin-associated disorder in a subject, the method comprising administering to the subject a therapeutically effective amount of the above-mentioned anti-α2 integrin antibody or the above-mentioned composition.

The invention further provides a method for inhibiting leukocyte binding to collagen comprising administering to a subject an amount of the above-mentioned anti-α2β1 integrin antibody or the above-mentioned composition effective to inhibit the binding of the leukocytes to collagen.

The invention further provides a use of the above mentioned humanized anti-α2 integrin antibody or the above-mentioned composition as a medicament.

The invention further provides a use of the above mentioned humanized anti-α2 integrin antibody or the above-mentioned composition for the treatment of an α2β1 integrin-associated disorder.

The invention further provides the above mentioned humanized anti-α2 integrin antibody or the above mentioned composition for use in a method for the treatment of an α2β1 integrin-associated disorder.

The invention further provides a use of the above mentioned humanized anti-α2 integrin antibody or the above-mentioned composition for the preparation of a medicament for the treatment of an α2β1 integrin-associated disorder.

The invention further provides an antibody comprising a variant human IgG Fc region which comprises amino acid substitution S324N replacing serine at amino acid position 324 of the parent antibody with asparagine, whereas the antibody exhibits improved complement dependent cytotoxicity (CDC) and improved antibody dependent cell mediated cytotoxicity (ADCC) as compared to the parent antibody.

DETAILED DESCRIPTION OF THE INVENTION

The present invention relates to humanized anti-α2 integrin antibodies which exhibit altered effector function compared to the parent humanized anti-α2 integrin antibody.

α2β1 integrin is a molecule comprised of an α2 integrin subunit from the family of alpha integrins, and a β1 integrin subunit from the family of beta integrins, and may be from any subject including a mammal, but preferably is from a human. The α2β1 integrin may be purified from any natural source, or may be produced synthetically (e.g., by use of recombinant DNA technology). The nucleic acid coding sequences for α2 integrin and for β1 integrin are described in Takada and Hemler J. Cell Biol. 109(1):397-407 (1989; GenBank submission X17033; subsequently updated to entry NM 002203) and Argraves, W. S, J. Cell. Biol. September 105(3):1183-90 (1987; Genbank submission X07979.1 and related sequences representing alternatively spliced variants), respectively.

The 'I' domain of the α2β1 integrin molecule refers to a region of this α2β1 integrin molecule within the α2 subunit, and is described, for example, in Kamata et al., J Biol. Chem. 269:9659-9663(1994); Emsley et al., J. Biol. Chem. 272:28512 (1997) and Cell 101:47 (2000). The I domain of α2 integrin contains a MIDAS type of ligand binding site (Metal Ion Dependent Adhesion Site) which has a requirement and a specificity for a given divalent cation to support ligand binding.

An α2 integrin-associated disorder includes a disorder, disease, or condition that involves. α2 integrin-dependent processes/function (e.g., binding, activity) that mediate aberrant cellular reactions within target tissue. An α2 integrin-associated disorder refers to a disorder, disease, symptom or condition that involves α2 integrin-dependent processes/function (e.g., binding, activity) that mediate aberrant cellular reactions within target tissue. Examples of α2 integrin-dependent processes involved in disease include collagen-dependent cellular responses such as those involved in increases in cytokine expression and proliferation, aspects of T-cell-, mast cell- and neutrophil-function, inflammatory disorders, mammary gland ductal morphogenesis, epidermal wound healing, and angiogenesis. Examples of α2 integrin-associated disorders include, but are not limited to, inflammatory diseases or disorders including but not limited to inflammatory bowel disease (such as Crohn's disease and ulcerative colitis), reactions to transplant (including transplant rejection), optic neuritis, spinal cord trauma, rheumatoid arthritis, multiple sclerosis (including treatment of neurological sequelae associated therewith as well as multiple sclerosis characterized by relapse), autoimmune diseases or disorders (including systemic lupus erythematosus (SLE), diabetes mellitus, Reynaud's syndrome, experimental autoimmune encephalomyelitis, Sjorgen's syndrome, scleroderma), juvenile onset diabetes, and disorders associated with abnormal or higher than normal angiogenesis (such as diabetic retinopathy, age related macula degeneration, cardiovascular disease, psoriasis, rheumatoid arthritis and cancer) as well as infections that induce an inflammatory response.

Treatment of an α2β1 integrin-associated disorder includes both therapeutic use and prophylactic or preventative use of the anti-α2 integrin antibodies described herein. Those in need of treatment include those already diagnosed with the disorder as well as those in which the onset of the disorder is to be prevented or delayed.

The terms "anti-α2 integrin antibodies" or "antibody that bind to α2" or "antibody that bind to α2 integrin subunit" or "anti-VLA-2 antibodies" are used synonymously herein and include antibodies, preferably humanized IgG antibodies, that bind to human α2 integrin, e.g. that bind to immobilized α2β1 with an affinity (Kd) of 50 nM or less, preferably 10 nM or less, more preferably 1 nM or less, in particular 0.5 nM or less.

By the terms "parent humanized anti-α2 integrin antibody" or "parent anti-α2 integrin antibody" or "parent anti-VLA-2 antibody" which are used synonymously herein are meant an antibody that binds human-α2 integrin, e.g. a humanized IgG1 anti-α2 integrin antibody which can be modified to comprise a variant human IgG1 heavy chain constant region. The parent humanized anti-α2 integrin antibody is identical to the antibody which comprises a variant human IgG1 heavy chain constant region, except for the amino acid modification in the human IgG1 heavy chain constant region and is usually an antibody with a native human IgG1 heavy chain constant region. The amino acid modification is preferably not isotopic.

The term "antibody" or "immunoglobulin" is used in the broadest sense, and covers monoclonal antibodies (including full length monoclonal antibodies), polyclonal antibodies, and multispecific antibodies, so long as they exhibit the desired biological activity. The term antibody or immunoglobulin comprises full length antibodies as well as fragments thereof which have antigen binding properties, i.e. which bind to α2 integrin. The term "antibody" includes a glycoprotein comprising at least two heavy (H) chains and two light (L) chains inter-connected by disulfide bonds, or an antigen binding fragment thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region (abbreviated herein as CL). The light chain constant region is comprised of one domain. The VH and VL regions can be further subdivided into regions of hypervariability, termed complementarity determining regions (CDR), interspersed with regions that are more conserved, termed framework regions (FR or FW). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the First component (C1q) of the classical complement system.

The term "full length antibody" as used herein includes the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains VL and CL, and each heavy chain comprising immunoglobulin domains VH, CH1 (C[gamma]1), CH2 (C[gamma]2), and CH3 (C[gamma]3). In some mammals, for example in camels and llamas, IgG antibodies may consist of only two heavy chains, each heavy chain comprising a variable domain attached to the Fc region.

The term "chimeric antibody" as used herein includes antibodies in which the variable region sequences are derived from one species and the constant region sequences are derived from another species, such as an antibody in which the variable region sequences are derived from a mouse antibody and the constant region sequences are derived from a human antibody.

The term "humanized antibody" as used herein includes antibodies in which CDR sequences derived from the germline of another mammalian species, such as a mouse, have been grafted onto human framework sequences. Additional framework region modifications may be made within the human framework sequences as well as within the CDR sequences derived from the germline of another mammalian species.

The term "human antibody" as used herein includes antibodies having variable regions, in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g. mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

A monoclonal antibody includes an antibody obtained from a population of substantially homogeneous antibodies, e.g., the individual antibodies comprising the population are identical except for possible naturally occurring mutations that may be present in minor amounts. Monoclonal antibodies are highly specific, being directed against a single antigenic site. Furthermore, in contrast to conventional (e.g., polyclonal) antibody preparations which typically include different antibodies directed against different determinants (e.g., epitopes) on an antigen, each monoclonal antibody is directed against at least a single determinant on the antigen. The modifier "monoclonal" indicates the character of the antibody as being obtained from a substantially homogeneous population of antibodies, and is not to be construed as requiring production of the antibody by any particular method. For example, monoclonal antibodies may be made by the hybridoma method first described by Kohler et al., Nature 256:495 (1975), or may be made by recombinant DNA methods (see, e.g., U.S. Pat. No. 4,816,567). Monoclonal antibodies may also be isolated from phage antibody libraries, for example, using the techniques described in Clackson et al., Nature 352:624-628 (1991) and Marks et al., J. Mol. Biol. 222:581-597 (1991). Monoclonal antibodies can also be isolated using the techniques described in U.S. Pat. Nos. 6,025,155 and 6,077,677 as well as U.S. Patent Application Publication Nos. 2002/0160970 and 2003/0083293 (see also, e.g., Lindenbaum, et al., Nucleic Acids Research 32 (21):0177 (2004)).

A hypervariable region includes the amino acid residues of an antibody which are responsible for antigen-binding. The hypervariable region comprises amino acid residues from a complementarity determining region or CDR (e.g., residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a hypervariable loop (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196: 901-917 (1987)). Framework or FR residues are those variable domain residues other than the hypervariable region residues. For antibodies described herein, the CDR and framework regions are identified based on the Kabat numbering system except that the CDR1 of the heavy chain is defined by Oxford Molecular's AbM definition as spanning residues 26 to 35. The Oxford Molecular's AbM antibody modeling software (http://people.cryst.cck.ac.uk/~ubc07s/) (Martin et al., Proc. Natl Acad. Sci. USA, 86, 9268-9272 (1989); Martin et al., Methods Enzymol., 203, 121-153 (1991); Pedersen et al., Immunomethods, 1, 126 (1992); and Rees et al., In Sternberg M. J. E. (ed.), *Protein Structure Prediction*. Oxford University Press, Oxford, 141-172. (1996)) combines the Kabat CDR and the Chothia hypervariable region numbering systems to define CDRs.

The term "amino acid modification" herein includes an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution R94K refers to a variant polypeptide, in this case a heavy chain variable framework region variant, in which the arginine at position 94 is replaced with a lysine. For the preceding example, 94K indicates the substitution of position 94 with a lysine. For the purposes herein, multiple substitutions are typically separated by a slash. For example, R94K/L78V refers to a double variant comprising the substitutions R94K and L78V. By "amino acid insertion" or "insertion" as used herein is meant the addition of an amino acid at a particular position in a parent polypeptide sequence. For example, insert –94 designates an insertion at position 94. By "amino acid deletion" or "deletion" as used herein is meant the removal of an amino acid at a particular position in a parent polypeptide sequence. For example, R94- designates the deletion of arginine at position 94.

For all immunoglobulin heavy chain constant region positions discussed in the present invention, numbering is according to the EU index as in Kabat (Kabat et al., 1991, Sequences of Proteins of Immunological Interest, 5th Ed., United States Public Health Service, National Institutes of Health, Bethesda, incorporated entirely by reference). The numbering of the immunoglobulin heavy chain constant region positions is referred herein as "numbering system set forth in Kabat" or "EU index as in Kabat" which is equivalently used herein and designates numbering according to the EU index as in Kabat. The "EU index as in Kabat" refers to the residue numbering of the human IgGI EU antibody, as described in Edelman et al., 1969, PNAS 63:78-85.

Antibodies are grouped into classes, also referred to as isotypes, as determined genetically by the constant region. Human constant light chains are classified as kappa (CK) and lambda (C[lambda]) light chains. Heavy chains are classified as mu, delta, gamma, alpha, or epsilon, and define the antibody's isotype as IgM, IgD, IgG, IgA, and IgE, respectively. The IgG class is the most commonly used for therapeutic purposes. In humans this class comprises subclasses IgG1, IgG2, IgG3, and IgG4. In mice this class comprises subclasses IgG1, IgG2a, IgG2b, IgG3. IgM has subclasses, including, but not limited to, IgM1 and IgM2. IgA has several subclasses, including but not limited to IgA1 and IgA2. Thus, "isotype" as used herein is meant any of the classes or subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE.

The term "Fc" or "Fc region", as used herein includes the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (C[gamma]2 and C[gamma]3) and the hinge between CgammaI (C[gamma]I) and Cgamma2 (C[gamma]2). Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, for example an antibody.

By "variant human IgG1 heavy chain constant region" as used herein is meant a human IgG1 heavy chain constant region that differs from a parent human IgG1 heavy chain constant region by virtue of at least one amino acid modification. By "Fc variant" or "variant Fc" or "variant human IgG1 Fc region" as used herein is meant an Fc sequence that differs from that of a parent Fc sequence by virtue of at least one amino acid modification. A variant human IgG1 heavy chain constant region or an Fc variant comprises one or more amino acid modifications relative to a parent Fc polypeptide, wherein said amino acid modification(s) provide one or more optimized properties. A variant human IgG1 heavy chain constant region or a Fc variant of the present invention differs in amino acid sequence from its parent IgG1 by virtue of at least one amino acid modification. Thus variant human IgG1 heavy chain constant region or Fc variants of the present invention have at least one amino acid modification compared to the parent. Alternatively, the variant human IgG1 heavy chain constant region of the present invention may have more than one amino acid modification as compared to the parent, e.g. may comprise conversion of a whole constant region immunoglobulin domain or, preferably, of an Fc region of one isotype in a different isotype, e.g. the conversion of the Fc region of the human IgG1 heavy chain constant region to an Fc region from human IgG3 resulting in an isotypic variant comprising the CHI from human IgG1, the hinge from human IgG1 and the Fc region from human IgG3. Modifications may be made genetically using molecular biology, or may be made enzymatically or chemically.

The Fc variants of the present invention may be substantially encoded by any allotype or isoallotype of any immunoglobulin gene. In a preferred embodiment, the Fc variants of the present invention find use in antibodies or Fc fusions that comprise IgG1 sequences that are classified as G1m(1), G1m(2), G1m(3), G1m(17), nG1m(1), nG1 m(2), and/or nG1 m(17). Thus in the context of an IgGI isotype, the Fc variants of the present invention may comprise a Lys (G1m (17)) or Arg (G1m(3)) at position 214, an Asp356/Leu358 (G1m(1)) or Glu356/Met358 (nG1 m(1)), and/or a Gly (G1m(2)) or Ala (nG1m(2)) at position 431.

The term "isotypic variant" as used herein includes an amino acid modification that converts at least one amino acid of one isotype, preferably at least one amino acid of the heavy chain constant region of one isotype, to the corresponding amino acid in a different, aligned isotype. The amino acid modification may comprise conversion of a whole constant region immunoglobulin domain or, preferably; of an Fc region of one isotype in a different isotype, e.g. the conversion of the Fc region of the human IgG1 heavy chain constant region to an Fc region from human IgG3 resulting in an isotypic variant comprising the CHI from human IgG1, the hinge from human IgG1 and the Fc region from human IgG3.

By "hinge" or "hinge region" or "antibody hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgGI) to 231 (A231 in IgGI), wherein the numbering is according to the EU index as in Kabat.

The term "effector function" as used herein includes a biochemical event that results from the interaction of an antibody Fc region with an Fc receptor or ligand. The term "effector function" as used herein includes phagocytosis, opsonization, cell binding, resetting, complement dependent cytotoxicity (CDC), C1q binding, binding affinity of the antibody for an Fc[gamma] receptor or antibody dependent cell mediated cytotoxicity (ADCC). Preferably the effector function is complement dependent cytotoxicity (CDC) and/or antibody dependent cell mediated cytotoxicity (ADCC). The effector function is measured by standard in vitro assays, which are known in the art and commercially available. Usually ADCC is measured by the lactate dehydrogenase (LDH)-releasing assay as described in Example 2 of the present application and CDC is measure by the cell-based assay described in Example 1 of the present application.

The term "alter effector function" or "exhibiting altered effector function" as used herein includes exhibition of enhanced effector function of an antibody, e.g. a humanized anti-α2 integrin antibody, comprising a variant human IgG1 heavy chain constant region compared to the parent antibody, i.e. the effector function of the antibody comprising a variant human IgG1 heavy chain constant region is more than 10%, preferably more than 20%, more preferably more than 30%, most preferably more than 50%, in particular more than 60%, most particular more than 70% higher than the effector function of the parent antibody.

The term "ADCC" or "antibody dependent cell-mediated cytotoxicity" as used herein includes the cell-mediated reaction wherein nonspecific cytotoxic cells that express Fc[gamma]Rs recognize bound antibody on a target cell and subsequently cause lysis of the target cell. In various aspects, the enhanced ADCC effector function can mean enhanced potency or enhanced efficacy. By "potency" as used in the experimental context is meant the concentration of antibody when a particular therapeutic effect is observed EC50 (half maximal effective concentration). By "efficacy" as used in the experimental context is meant the maximal possible effector function at saturating levels of antibody.

The term "CDC" or "complement dependent cytotoxicity" as used herein includes the reaction wherein one or more complement protein components recognize bound antibody on a target cell and subsequently cause lysis of the target cell.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc. Preferably the subject is human.

A cytotoxic agent includes a substance that inhibits or prevents the function of cells and/or causes destruction of cells. The can include radioactive isotopes (e.g., $^{131}$I, $^{125}$I, $^{90}$Y and $^{186}$Re), chemotherapeutic agents, and toxins such as enzymatically active toxins of bacterial, fungal, plant or animal origin, or fragments thereof. A non-cytotoxic agent refers to a substance that does not inhibit or prevent function of cells and/or does not cause destruction of cells. A non-cytotoxic agent may include an agent that can be activated to become cytotoxic. A non-cytotoxic agent may include a bead, liposome, matrix or particle (see, e.g., U.S. Patent Publications 2003/0028071 and 2003/0032995 which are incorporated by reference herein). Such agents may be conjugated, coupled, linked or associated with an anti-α2β1 integrin antibody as described herein.

A chemotherapeutic agent refers to a chemical compound useful in the treatment of cancer. Examples of chemotherapeutic agents include but are not limited to Adriamycin, Doxorubicin, 5-Fluorouracil, Cytosine arabinoside ("Ara-C"), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see U.S. Pat. No. 4,675,187), Melphalan and other related nitrogen mustards.

An isolated nucleic acid molecule refers to a nucleic acid molecule that is identified and separated from at least one contaminant nucleic acid molecule with which it is ordinarily associated in the source e.g. in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

Cell, cell line, and cell culture are often used interchangeably and all such designations include progeny. Transformants and transformed cells (e.g., obtained by transfection, transformation or transduction of nucleic acids, vectors, virus, etc.) include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Humanized Anti-α2 Integrin Antibodies Comprising a Variant Human IgG1 Heavy Constant Domain The present invention provides a humanized anti-α2 integrin antibody comprising a heavy chain variable region, a light chain variable region, a human light chain constant region and a variant human IgG1 heavy chain constant region, whereas the variant human IgG1 heavy chain constant region comprises at least one amino acid modification relative to the human IgG1 heavy constant region of the parent humanized anti-α2 integrin antibody, and whereas the antibody exhibits altered effector function compared to the parent humanized anti-α2 integrin antibody.

In one aspect, the present disclosure provides a humanized anti-α2 integrin antibody comprising a heavy chain variable region, a light chain variable region, a human light chain constant region and a variant human IgG1 heavy constant region, wherein the variant human IgG1 heavy chain constant region is an isotypic variant comprising the CH1 from human IgG1, the hinge from human IgG1 and the Fc region from human IgG3.

In one embodiment the isotypic variant human IgG1 heavy constant region comprises SEQ ID NO: 35.

In one aspect, the present disclosure provides a humanized anti-α2 integrin antibody comprising a heavy chain variable region, a light chain variable region, a human light chain constant region and a variant human IgG1 heavy constant region, wherein the variant human IgG1 heavy chain constant region is an isotypic variant comprising the CH1 from human IgG3, the hinge from human IgG1 and the Fc region from human IgG3.

In one embodiment the isotypic variant human IgG1 heavy constant region comprises SEQ ID NO: 36.

In one aspect, the present disclosure provides a humanized anti-α2 integrin antibody comprising a heavy chain variable region, a light chain variable region, a human light chain constant region and a variant human IgG1 heavy constant region, wherein the variant human IgG1 heavy chain constant region comprises a variant human IgG1 Fc region which comprises at least one amino acid modification relative to the human IgG Fc region of the parent humanized anti-α2 integrin antibody.

In one embodiment, the amino acid modification comprises an amino acid substitution at amino acid position selected from the group consisting of 269, 298, and 324, preferably an amino acid substitution at amino acid position 298 and/or 324, wherein the amino acid position of each group member is indicated utilizing the numbering system set forth in Kabat.

In another embodiment, the amino acid modification comprises an amino acid substitution selected from the group consisting of E269D, S298A, and S324N, preferably amino acid substitutions S298A and/or S324N, wherein the amino acid position of each group member is indicated utilizing the numbering system set forth in Kabat.

In another embodiment, the amino acid modification comprises a combination of amino acid substitutions at amino acid position selected from the group consisting of 269/298, 269/324, 298/324, and 269/298/324, preferably 298/324, or 269/298/324, wherein the amino acid position of each group member is indicated utilizing the numbering system set forth in Kabat.

In another embodiment, the amino acid modification comprises a combination of amino acid substitutions selected from the group consisting of E269D/S298A, E269D/S324N, S298A/S324N, and E269D/S298A/S324N, preferably S298A/S324N or E269D/S298A/S324N, wherein the amino acid position of each group member is indicated utilizing the numbering system set forth in Kabat.

In one embodiment the variant human IgG1 Fc region comprises a sequence selected from the group consisting of SEQ ID NOs: 37-43.

The effector function altered is usually complement dependent cytotoxicity (CDC) and/or C1q binding and/or antibody dependent cell mediated cytotoxicity (ADCC) and/or binding affinity of the antibody for an Fc[gamma] receptor, preferably complement dependent cytotoxicity (CDC) and/or antibody dependent cell mediated cytotoxicity (ADCC). CDC, C1q binding, ADCC, and binding affinity of the antibody for an Fc[gamma] receptor are measured by standard in vitro assays, which are known in the art and commercially available. Usually ADCC is measured by the lactate dehydrogenase (LDH)-releasing assay as described e.g. in Example 2 of the present application and CDC is measure by the cell-based assay described e.g. in Example 1 of the present application.

Preferably the humanized anti-α2 integrin antibody of the present disclosure comprising the variant human IgG1 heavy chain constant region exhibits improved CDC in an in vitro assay as described above compared to the parent humanized antibody. "Exhibition of improved CDC" or "exhibiting improved CDC" as used herein includes a) exhibition of enhanced CDC compared to the parent antibody, i.e. the parent humanized anti-α2 integrin antibody already exhibits CDC which is enhanced by the amino acid modification of the human IgG1 heavy chain constant region and b) de novo exhibition of CDC compared to the parent humanized anti-α2 integrin antibody, i.e. the parent humanized anti-α2 integrin antibody does not exhibit CDC, thus CDC has been introduced de novo by the amino acid modification of the human IgG1 heavy chain constant region.

Thus in a further aspect the present disclosure provides a humanized anti-α2 integrin antibody comprising a heavy chain variable region, a light chain variable region, a human light chain constant region and a variant human IgG1 heavy constant region, whereas the variant human IgG1 heavy chain constant region comprises at least one amino acid modification relative to the human IgG1 heavy chain constant region of the parent humanized anti-α2 integrin antibody, and whereas the antibody exhibits improved complement dependent cytotoxicity (CDC) as compared to the parent humanized antibody. A preferred variant human IgG1 heavy chain constant region of the humanized anti-α2 integrin antibody which exhibits improved complement dependent cytotoxicity (CDC) as compared to the parent humanized antibody comprises a variant human IgG1 Fc region which comprises an amino acid substitution selected from the group consisting of S324N, S298A/S324N, and E269D/S298A/S324N, more preferably the variant human IgG1 Fc region comprises the amino acid sequence selected from the group consisting of SEQ ID NO: 39, 42 and 43.

In one embodiment, the humanized anti-α2 integrin antibody comprising the variant human IgG1 heavy chain constant region which exhibits improved complement dependent cytotoxicity (CDC) as compared to the parent humanized anti-α2 integrin antibody exhibits antibody dependent cell mediated cytotoxicity (ADCC) equivalent to the parent humanized antibody. Exhibition of ADCC equivalent to the parent humanized antibody includes an ADCC of ±50%, preferably ±40%, more preferably ±30%, most preferably ±20%, in particular ±10%, of the ADCC of the parent humanized antibody. It is known that IgG1 antibodies, e.g humanized IgG1 anti-α2 integrin antibodies as parent antibodies exhibit ADCC. It is not predictable, however, if a modification, e.g. a substitution of an amino acid which provides for improved complement dependent cytotoxicity (CDC) of the IgG1 heavy chain constant region does have an impact on ADCC. Thus the humanized anti-α2 integrin antibodies of the present invention which comprises a variant human IgG1 heavy chain constant region which exhibits improved CDC surprisingly exhibits ADCC equivalent to the parent humanized antibody.

In a further aspect the present disclosure provides a humanized anti-α2 integrin antibody comprising a heavy chain variable region, a light chain variable region, a human light chain constant region and a variant human IgG1 heavy constant region, wherein the variant human IgG1 heavy chain constant region comprises a variant human IgG1 Fc region which comprises at least one amino acid modification relative to the human IgG Fc region of the parent humanized anti-α2 integrin antibody, and whereas the antibody exhibits improved antibody dependent cell mediated cytotoxicity (ADCC) as compared to the parent humanized antibody. A preferred variant human IgG1 heavy chain constant region of the humanized anti-α2 integrin antibody which exhibits improved antibody dependent cell mediated cytotoxicity (ADCC) as compared to the parent humanized antibody comprises a variant human IgG1 Fc region which comprises an amino acid substitution selected from the group consisting of E269D, S298A, S298A/S324N, and E269D/S298A/S324N, more preferably the variant human IgG1 Fc region comprises the amino acid sequence selected from the group consisting of SEQ ID NO: 37, 38, 42 and 43.

In a further aspect the present disclosure provides a humanized anti-α2 integrin antibody comprising a heavy chain variable region, a light chain variable region, a human light chain constant region and a variant human IgG1 heavy constant region, wherein the variant human IgG1 heavy chain constant region comprises a variant human IgG1 Fc region which comprises at least one amino acid modification relative to the human IgG Fc region of the parent humanized anti-α2 integrin antibody, wherein the amino acid modification is amino acid substitution S298A/S324N or E269D/S298A/S324N, whereas the antibody exhibits improved complement dependent cytotoxicity (CDC) and improved antibody dependent cell mediated cytotoxicity (ADCC) as compared to the parent humanized anti-α2 integrin antibody.

Antibodies of the present invention have been constructed comprising CDRs from both the heavy chain variable and light chain variable regions of the murine monoclonal antibody clone BHA2.1 (Hangan et al., Cancer Res. 56:3142-3149 (1996)). Preferred starting materials for constructing antibodies are anti-α2 integrin antibodies such as those secreted by the BHA2.1 hybridoma (e.g., TMC-2206) that are function-blocking antibodies directed against human α2 integrin and are dependent for binding and activity on the presence of an intact I-domain within the targeted α2 integrin. Preferred are humanized antibodies with the epitope specificity of TMC-2206 (or BHA2.1), including antibodies which bind to the inactive conformation of the α2 integrin molecule, and/or do not act as ligand mimetics. Preferred are humanized antibodies with the epitope specificity of TMC-2206 (or BHA2.1) that, although they interact with α2β1 integrin present on both leukocytes and platelets, do not cause platelet activation, impair aggregation of activated platelets on collagen, have minimal or no effect on bleeding and/or are not associated with bleeding complications at administered concentrations, including therapeutic doses in vivo.

Thus also provided is the above-mentioned humanized anti-α2 integrin antibody comprising a heavy chain variable region comprising HCDR1 comprising the amino acid sequence GFSLTNYGIH (SEQ ID NO:1), HCDR2 comprising the amino acid sequence VIWARGFTNYNSALMS (SEQ ID NO:2) and HCDR3 comprising the amino acid sequence ANDGVYYAMDY (SEQ ID NO:3).

Also provided is the above-mentioned humanized anti-α2 integrin antibody comprising a light chain variable region comprising LCDR1 comprising the amino acid sequence SAQSSVNYIH (SEQ ID NO:4), LCDR2 comprising the amino acid sequence DTSKLAS (SEQ ID NO:5) and LCDR3 comprising the amino acid sequence QQWTTNPLT (SEQ ID NO:6).

Also provided is the above-mentioned humanized anti-α2 integrin antibody comprising a heavy chain variable region comprising HCDR1 comprising the amino acid sequence GFSLTNYGIH (SEQ ID NO:1), HCDR2 comprising the amino acid sequence VIWARGFTNYNSALMS (SEQ ID NO:2) and HCDR3 comprising the amino acid sequence ANDGVYYAMDY (SEQ ID NO:3); and/or a light chain variable region comprising LCDR1 comprising the amino acid sequence SAQSSVNYIH (SEQ ID NO:4), LCDR2 comprising the amino acid sequence DTSKLAS (SEQ ID NO:5) and LCDR3 comprising the amino acid sequence QQWTTNPLT (SEQ ID NO:6).

In an embodiment, the above-mentioned heavy chain variable region comprises the amino acid sequence of SEQ ID NO: 7.

In an embodiment, the above-mentioned heavy chain variable region comprises the amino acid sequence of SEQ ID NO: 7 in which (a) position 71 is Lys, (b) position 73 is Asn, (c) position 78 is Val, or (d) any combination of (a)-(c).

In an embodiment, the above-mentioned heavy chain variable region comprises an amino acid sequence selected from SEQ ID NOs:8-19.

In an embodiment, the above-mentioned heavy chain variable region comprises the amino acid sequence of SEQ ID NO: 17.

In an embodiment, the above-mentioned heavy chain variable region further comprises a FW4 region comprising the amino acid sequence WGQGTLVTVSS (SEQ ID NO:20).

In an embodiment, the above-mentioned light chain variable region comprises the amino acid sequence of SEQ ID NO: 21.

In an embodiment, the above-mentioned light chain variable region comprises the amino acid sequence of SEQ ID NO: 21 in which (a) position 2 is Phe, (b) position 45 is Lys, (c) position 48 is Tyr, or (d) any combination of (a)-(c).

In an embodiment, the above-mentioned the light chain variable region comprises an amino acid sequence selected from SEQ ID NOs: 22-33.

In an embodiment, the above-mentioned light chain variable region comprises the amino acid sequence of SEQ. ID NO: 30.

In an embodiment, the above-mentioned light chain variable region further comprises a FW4 region comprising the amino acids sequence FGQGTKVEIK (SEQ ID NO: 34).

Further provided is the above-mentioned humanized anti-α2 integrin antibody comprising the above-mentioned variant human IgG1 heavy chain constant region, the above-mentioned heavy and light chain variable regions and a human light chain constant region.

Thus in a further embodiment, the anti-α2 integrin antibody comprises a heavy chain comprising SEQ ID NO: 47 and a light chain comprising SEQ ID NO: 56.

In a further embodiment, the anti-α2 integrin antibody comprises a heavy chain comprising SEQ ID NO: 48 and a light chain comprising SEQ ID NO: 56.

In a further embodiment, the anti-α2 integrin antibody comprises a heavy chain selected from the group consisting of SEQ ID NO: 49-55 and a light chain comprising SEQ ID NO: 56.

Further provided is an antibody comprising a variant human IgG Fc region which comprises amino acid substitution S324N replacing serine at amino acid position 324 of the parent antibody with asparagine, whereas the antibody exhibits improved complement dependent cytotoxicity (CDC).

Further provided is an antibody comprising a variant human IgG Fc region which comprises amino acid substitution S324N replacing serine at amino acid position 324 of the parent antibody with asparagine, whereas the antibody exhibits improved complement dependent cytotoxicity (CDC) and improved antibody dependent cell mediated cytotoxicity (ADCC) as compared to the parent antibody. The antibody may further comprise amino acid substitution E269D replacing glutamate at amino acid position 269 of the parent antibody with aspartate and/or substitution S298A replacing serine at amino acid position 298 of the parent antibody with alanine. The antibody can be selected from the group consisting of a chimeric antibody, a humanized antibody and a fully human antibody The antibody is preferably a humanized antibody, more preferably a humanized anti-α2 integrin antibody.

In an embodiment, the above-mentioned humanized anti-α2 integrin antibody recognizes the I domain of human α2 integrin.

In an embodiment, the above-mentioned humanized anti-α2 integrin antibody binds α2β1 integrin.

In an embodiment, the above-mentioned humanized anti-α2 integrin antibody inhibits binding of α2 or α2β1 integrin to an α2β1 integrin ligand. Usually the α2β1 integrin ligand is selected from collagen, laminin, Echovirus-1, decorin, E-cadherin, matrix metalloproteinase I (MMP-I), endorepellin, collectin and C1q complement protein and is preferably collagen.

Also provided is an isolated nucleic acid encoding the above-mentioned humanized anti-α2 integrin antibody, a vector comprising the nucleic acid and a host cell comprising the nucleic acid or the vector.

Also provided is a composition comprising the above-mentioned humanized anti-α2 integrin antibody and a pharmaceutically acceptable carrier.

Also provided is a method of treating an α2β1 integrin-associated disorder in a subject, the method comprising administering to the subject a therapeutically effective amount of the above-mentioned humanized anti-α2 integrin antibody or the above-mentioned composition. The α2β1 integrin-associated disorder includes inflammatory disease, autoimmune disease and a disease characterized by abnormal or increased angiogenesis, in particular inflammatory bowel disease, Crohn's disease, ulcerative colitis, reactions to transplant, optical neuritis, spinal cord trauma, rheumatoid arthritis, systemic lupus erythematosus (SLE), diabetes mellitus, multiple sclerosis, Reynaud's syndrome, experimental autoimmune encephalomyelitis, Sjorgen's syndrome, scleroderma, juvenile onset diabetes, diabetic retinopathy, age related macular degeneration, cardiovascular disease, psoriasis, cancer as well as infections that induce an inflammatory response more particular multiple sclerosis, rheumatoid arthritis, optical neuritis and spinal cord trauma.

Cancers which can be treated by the above-mentioned humanized anti-α2 integrin antibody or the above-mentioned composition are selected from the group consisting of squamous cell cancer, lung cancer including small-cell lung cancer, non-small cell lung cancer, adenocarcinoma of the lung, and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's Macroglobulinemia; chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema such as that associated with brain tumors, Meigs' syndrome, melanoma, mesothelioma, multiple myeloma, fibrosarcoma, osteosarcoma, and epidermoid carcinoma. Cancers which are preferably treated using the anti-α2 integrin antibodies described herein are selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, melanoma, ovarian cancer, mesothelioma, and multiple myeloma. The cancerous conditions amendible for treatment of the invention include metastatic cancers. Thus even more preferred are cancers selected from the group consisting of breast cancer, colorectal cancer, rectal cancer, non-small cell lung cancer, non-Hodgkins lymphoma (NHL), renal cell cancer, prostate cancer, metastatic prostate cancer, liver cancer, pancreatic cancer, soft-tissue sarcoma, kaposi's sarcoma, carcinoid carcinoma, head and neck cancer, melanoma, ovarian cancer, mesothelioma, multiple myeloma, metastatic colorectal and metastatic breast cancer. Particular preferred are cancers selected from the group consisting of non-small cell lung cancer, pancreatic cancer, glioblastoma, cervical cancer, ovarian cancer, liver cancer, breast cancer, colon cancer, colorectal cancer, kidney cancer, prostate cancer, metastatic prostate cancer, mesothelioma, fibrosarcoma, osteosarcoma, epidermoid carcinoma, metastatic colorectal, metastatic prostate and metastatic breast cancer. More particular preferred are cancers selected from the group consisting of non-small cell lung cancer, pancreatic cancer, glioblastoma, liver cancer, breast cancer, colon cancer, colorectal cancer, kidney cancer, prostate cancer, mesothelioma, fibrosarcoma, metastatic colorectal, metastatic prostate and metastatic breast cancer. Even more particular preferred are cancers selected from the group consisting of pancreatic cancer, breast cancer, colon cancer, colorectal cancer, non-small cell lung cancer, fibrosarcoma, metastatic colorectal, prostate cancer, metastatic prostate cancer and metastatic breast cancer. Most particular preferred are cancers selected from the group consisting of pancreatic cancer, breast cancer, colon cancer, colorectal cancer, non-small cell lung cancer, and fibrosarcoma. Most preferred are pancreatic cancer, breast cancer or metastatic breast cancer, with a particular preference to pancreatic cancer. Equally most particular preferred is prostate cancer or metastatic prostate cancer. "Breast cancer" as referred herein include mammary adenocarcinoma. The method of the present invention is particularly suitable for the treatment of vascularized tumors.

Preferably the method is not associated with (a) platelet activation, (b) platelet aggregation, (c) a decrease in circulating platelet count, (d) bleeding complications, or (e) any combination of (a) to (d).

Also provided is a method for inhibiting leukocyte binding to collagen comprising administering to a subject an amount of the above-mentioned humanized anti-α2 integrin antibody effective to inhibit the binding of the leukocytes to collagen.

Also provided is a kit comprising the above-mentioned humanized anti-α2 integrin antibody or the above-mentioned composition according and instructions for the treatment of an α2β1 integrin-associated disorder.

Construction of Humanized Anti-α2 Integrin Antibodies and Conjugates

Antibodies may be constructed wherein the human acceptor molecule for the light chain variable region is selected based on homology considerations between potential acceptor molecule variable regions and with the light chain variable region of the murine antibody. Germline candidate human acceptor molecules are preferred to reduce potential immunogenicity. Germline databases are made up of antibody sequences that read through the end of the heavy chain FW3 region and partially into the CDR3 sequence. For selection of a FW4 region, it is preferred to search databases of mature antibody sequences which have been derived from the selected germline molecule, and also preferred to select a reasonably homologous FW4 region for use in the recombinant antibody molecule. Human acceptor molecules are preferably selected from the same light chain class as the murine donor molecule, and of the same canonical structural class of the variable region of the murine donor molecule. Secondary considerations for selection of the human acceptor molecule for the light chain variable region include homology in CDR length between the murine donor molecule and the human acceptor molecule. Human acceptor antibody molecules are preferably selected by homology searches to the V-BASE database, and other databases such as the Kabat and the public NCBI databases may be used as well. For humanized anti-α2 integrin antibodies with the same or similar epitope specificity and/or functional properties as TMC-2206, a preferred light chain human acceptor molecule is the germline antibody sequence A14 for the FW 1-3 region and the sequence FGQGTKVEIK for FW4 (SEQ ID NO:34) which represents a common FW-4 of mature kappa 1 light chains (e.g., light chain sequence AAB24132 (NCBI entry gi/259596/gb/AAB24132).

Antibodies may be constructed wherein the human acceptor molecule for the heavy chain variable region is selected based on homology considerations between potential acceptor molecule variable regions and the heavy chain variable region of the murine antibody. Germline candidate human acceptor molecules are preferred to reduce potential antigenicity. Germline databases are made up of antibody sequences that read through the end of the heavy chain FW3 region and partially into the CDR3 sequence. For selection of a FW4 region, it is preferred to search databases of mature antibody sequences which have been derived from the selected germline molecule, and also preferred to select a reasonably homologous FW4 region for use in the recombinant antibody molecule. Human acceptor molecules are preferably selected from the same heavy chain class as the murine donor molecule, and of the same canonical structural class of the variable region of the murine donor molecule. Secondary considerations for selection of the human acceptor molecule for the heavy chain variable region include homology in CDR length between the murine donor molecule and the human acceptor molecule. Human acceptor antibody molecules are preferably selected by homology search to the V-BASE database, although other databases such as the Kabat and the public NCBI databases may be used as well. For anti-α2 integrin antibodies with the same or similar epitope specificity and/or functional properties as TMC-2206, a preferred heavy chain acceptor molecule is the germline antibody sequence 4-59 for the FW 1-3 region and antibody, CAA48104.1 (NCBI entry, gi/33583/emb/CAA48104.1) a mature antibody derived from the 4-59 germline sequence for the FW 4 region (SEQ ID NO:20).

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025,155 and 6,077,677 as well as U.S. Patent Application Publication Nos. 2002/0160970 and 2003/0083293 (see also, e.g., Lindenbaum, et al., Nucleic Acids Research 32 (21):0177 (2004)).

Amino acid sequence variants of humanized anti-α2β1 integrin antibody are prepared by introducing appropriate nucleotide changes into a humanized anti-α2β1 integrin antibody DNA, or by peptide synthesis. Such variants include, for example, deletions from, and/or insertions into and/or substitutions of, residues within the amino acid sequences shown for the anti-α2 integrin antibody of the present invention. Any combination of amino acid deletion, insertion, and substitution is made to arrive at the final construct, provided that the final construct possesses the desired characteristics. The amino acid changes also may alter post-translational processes of the humanized anti-α2 integrin antibody, such as changing the number or position of glycosylation sites.

There are a number of methods used to make antibodies human or human-like (e.g., "humanization"). Approaches to humanize antibodies have varied over the years. One approach was to generate murine variable regions fused to human constant regions, so-called murine-human Fc chimeras (see, e.g., Morrison et al, Proc. Natl. Acad. Sci. USA 81:6851-6855 (1984); U.S. Pat. No. 5,807,715). Another approach exploited the fact that CDRs could be readily identified based on their hypervariable nature (Kabat et al, J. Biol. Chem. 252:6609-6616 (1977)), Kabat, Adv. Protein Chem. 32:1-75 (1978)) and canonical structure (Chothia and Lesk, J. Mol. Biol. 196(4):901-17 (1987); Lazakani et al., J. Mol. Biol. 272:929 (1997) and humanized by grafting just the non-human CDR regions (referred to as donor CDRs) onto a human framework (referred to as acceptor frameworks) as shown, for example by Jones et al., Nature 321(6069):522-5 (1986); (see, e.g., U.S. Pat. Nos. 5,225,539; 6,548,640). The six CDR loops are presented in a cluster, and based on crystallographic analysis, critical framework residues within the so-called "Vernier" zone flanking the CDRs or in the heavy-light chain interface can be readily identified (see, e.g., Chothia and Lesk, J. Mol. Biol. 196(4):901-17 (1987); Chothia et al., J. Mol. Biol. 186(3):651-63 (1985); Chothia et al., Nature 342(6252): 877-83 (1989)). These residues can be back-mutated to the murine residue to restore the correct relative orientation of the six CDRs (see, e.g., Verhoyen et al., Science 239(4847): 1534-6 (1988); Reichman et al., Nature 332(6162):323-7 (1988); Tempest et al., Biotechnology (NY) 9(3):266-71 (1991)). Since variable regions can be classified in families that bear relatively high homology between mouse and human (reviewed in e.g., Pascual and Capra Adv. Immunol. 49:1-74 (1991)), these early studies also indicated that the potential for loss in affinity could be minimized in the grafted antibody by selecting the human germline sequence with the highest homology to the murine antibody of interest for use as the human acceptor molecule (see, e.g., U.S. Pat. No. 5,225,539; Verhoyen et al., Science 239(4847):1534-6 (1988)).

Methods for humanizing a non-human α2 integrin antibody are described e.g. in WO2007/056858. In order to humanize an anti-α2 integrin antibody, the nonhuman antibody starting material is obtained, including by preparation from immunization or by purchase of commercially available antibodies. Exemplary techniques for humanizing antibodies used in the present invention e.g for humanizing TMC-2206 are described in WO2007/056858.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic: trp, tyr, phe. Any cysteine residue not involved in maintaining the proper confirmation of a humanized anti-α2 integrin antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Another type of amino acid variant of the antibody alters the original glycosylation pattern of the antibody. By altering is meant deleting one or more carbohydrate moieties found in the antibody and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that it contains or lacks one or more of the above-described tripeptide sequences (for N-linked glycosylation sites). The alteration may also be made by the addition of, substitution by, or deletion of, one or more serine or threonine residues to the sequence of the original antibody (for O-linked glycosylation sites). Nucleic acid molecules encoding amino acid sequence variants of humanized anti-α2 integrin antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, or cassette mutagenesis of an earlier prepared variant or a non-variant version of humanized anti-α2 integrin antibody.

Ordinarily, amino acid sequence variants of a humanized anti-α2 integrin antibody, will have an amino acid sequence having at least 75% amino acid sequence identity with the original humanized antibody amino acid sequences of either the heavy or the light chain (e.g., variable region sequences as in SEQ ID NO:17 or SEQ ID NO:30, respectively), more preferably at least 80%, more preferably at least 85%, more preferably at least 90%, and most preferably at least 95%, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to this sequence is defined herein as the percentage of amino acid residues in the candidate sequence that are identical with the humanized anti-α2 integrin residues, after aligning the sequences and introducing gaps, if necessary, to achieve the maximum percent sequence identity, and not considering any conservative substitutions (as described above) as part of the sequence identity. None of N-terminal, C-terminal, or internal extensions, deletions, or insertions into the antibody sequence shall be construed as affecting sequence identity or homology. Thus sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences, or along a predetermined portion of one or both sequences). The programs provide a default opening penalty and a default gap penalty, and a scoring matrix such as PAM250 (a standard scoring matrix; see Dayhoff et al., in Atlas of Protein Sequence and Structure, vol 5, supp. 3 (1978)) can be used in conjunction with the computer program. For example, the percent identity can the be calculated as: the total number of identical matches multiplied by 100 and then divided by the sum of the length of the longer sequence within the matched span and the number of gaps introduced into the longer sequences in order to align the two sequences.

In some embodiments, it may be desirable to generate multispecific (e.g., bispecific) humanized anti-α2 integrin antibodies having binding specificities for at least two different epitopes. Exemplary bispecific antibodies (e.g., with two different binding arms) may bind to two different epitopes of the α2β1 integrin protein. Alternately, an anti-α2 integrin arm may be combined with an arm which binds to a triggering molecule on a leukocyte such as a T-cell receptor molecule (e.g., CD2 or CD3), or Fc receptors for IgG (FcγR), such as FcγR1 (CD64), FcγRII (CD32) and FcγRIII (CD16) so as to focus cellular defense mechanisms on a cell which has α2β1 integrin bound to its surface. Bispecific antibodies can be used to localized cytotoxic agents to cells with α2β1 integrin bound to their surface.

These antibodies possess a α2β1 integrin binding arm and an arm which binds the cytotoxic agent (e.g., gelonin, saporin, anti-interferon alpha, vinca alkaloid, ricin A chain, or radioisotope hapten).

According to another approach for making bispecific antibodies, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains are replaced with larger side chains (e.g., tyrosine or tryptophan). Compensatory cavities of identical or smaller size to the large side chain(s) are created on the interface of the second antibody by replacing large amino acid side chains with smaller ones (e.g., alanine or threonine). This provides a mechanism for increasing the yield of the heterodimers over other unwanted end-products such as homodimers (see, e.g., WO96/27011).

Bispecific antibodies include cross-linked or heteroconjugate antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed, for example, in U.S. Pat. No. 4,676,980 along with a number of cross-linking techniques.

Antibodies with more than two valencies are contemplated. For example, trispecific antibodies can be prepared (see, e.g., Tutt et al., J. Immunol. 147:60 (1991)).

Immunoconjugates comprising a humanized anti-α2 integrin antibody conjugated to a moiety, e.g., a molecule, composition, complex, or agent, for example a cytotoxic agent such as a chemotherapeutic agent, toxin (e.g., an enzymatically active toxin of bacterial, fungal, plant or animal origin, or fragments thereof), or a radioactive isotope (e.g., a radioconjugate), for the targeting of the agent to an anti-α2 integrin-expressing cell, tissue or organ. Such an immunoconjugate may be used in a method of targeting the moiety or agent to a particular site of action characterized by the presence of α2 or α2β1 integrin.

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, Phytolaca americana proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin or the tricothecenes. A variety of radionuclides are available for the production of radioconjugated anti-alpha 2 integrin antibodies. Examples include $^{212}$Bi, $^{131}$In, $^{90}$Y or $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as gluteraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), or bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionuclide to the antibody (see, e.g., WO94/11026).

In another embodiment, the antibody may be conjugated to a receptor (such as streptavidin) for utilization in pretargeting α2 integrin-expressing cell, tissue or organ wherein the antibody-receptor conjugate is administered to the patient, followed by removal of unbound conjugate from the circulation using a clearing agent and then administration of a ligand (e.g., avidin) which is conjugated to an agent, for example a cytotoxic agent (e.g., a radio-nuclide).

The anti-α2 integrin antibodies disclosed herein may also be formulated as immunoliposomes. Liposomes containing the antibody are prepared by methods known in the art, such as described in Epstein et al., Proc. Natl. Acad. Sci. USA 82: 3688 (1985); Hwang et al., Proc. Natl. Acad. Sci. USA 77: 4030 (1980); and U.S. Pat. Nos. 4,485,045 and 4,544,545. Liposomes with enhanced circulation time are disclosed in U.S. Pat. No. 5,013,556.

Humanized anti-α2 integrin antibodies may also be used in Antibody Directed Enzyme Prodrug Therapy (ADEPT) by conjugating the antibody to a prodrug-activating enzyme which converts a prodrug (e.g., a peptidyl chemotherapeutic agent, see, e.g., WO81/01145) to an active drug. (see, e.g., WO88/07378 and U.S. Pat. No. 4,975,278).

Enzymes may be covalently bound to the anti-α2 integrin antibodies by techniques well known in the art, including the use of the heterobifunctional crosslinking reagents discussed above. Alternatively, fusion proteins comprising at least the antigen binding region of an anti-α2 integrin antibody linked to at least a functionally active portion of an enzyme can be constructed using recombinant DNA techniques well known in the art (see, e.g., Neuberger et al., Nature 312: 604-608 (1984)).

Covalent modifications of the humanized anti-α2 integrin antibodies may be made, for example, by chemical synthesis or by enzymatic or chemical cleavage of the antibody. Other types of covalent modifications of the antibody are introduced into the molecule by reacting targeted amino acid residues of the antibody with an organic derivatizing agent that is capable of reacting with selected side chains or the N- or C-terminal residues. Cysteinyl residues, for example, most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl) propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues, for example, are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0. Lysinyl and amino-terminal residues, for example, are reacted with succinic or other carboxylic acid anhydrides. Derivatization with these agents, has the effect of reversing the charge of the lysinyl residues. Other suitable reagents for deriyatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate. Arginyl residues, for example, are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group. Tyrosyl residues, for example, are specifically modified with particular interest in introducing spectral labels into tyrosyl residues by reaction with aromatic diazonium compounds or tetranitromethane. Most commonly, N-acetylimidizole and tetranitromethane are used to form P-acetyl tyrosyl species and 3-nitro derivatives, respectively. Tyrosyl residues are iodinated using $^{125}I$ or $^{131}I$ to prepare labeled proteins for use in radioimmunoassay. Carboxyl side groups, for example, aspartyl or glutamyl, are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions. Glutaminyl and asparaginyl residues are frequently deamidated to the corresponding glutamyl and aspartyl residues, respectively. These residues are deamidated under neutral or basic conditions. The deamidated form of these residues falls within the scope of this invention. Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine (see, e.g., WO87/05330; Aplin and Wriston, CRC Crit. Rev. Biochem., pp. 259-306 (1981)).

Removal of any carbohydrate moieties present on the antibody may be accomplished, for example, chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact (see, e.g., Hakimuddin, et al., Arch. Biochem. Biophys. 259: 52 (1987); Edge et al., Anal. Biochem., 118: 131 (1981)). Enzymatic cleavage of carbohydrate moieties on antibodies can be achieved by the use of a variety of endo- and exo-glycosidases, (see, e.g., Thotakura et al., Meth. Enzymol. 138: 350 (1987)).

Another type of covalent modification of the antibody comprises linking the antibody to one of a variety of nonproteinaceous polymers, such as polyethylene glycol, polypropylene glycol, or polyoxyalkylenes (see, e.g., U.S. Pat. Nos. 4,640,835; 4,496,689; 4,301,144; 4,670,417; 4,791,192 or 4,179,337).

Isolated nucleic acid(s) encoding a humanized anti-α2 integrin antibody, as well as vectors and host cells comprising the nucleic acid, and recombinant techniques for the production of the antibody are described herein. For recombinant production of the antibody, the nucleic acid(s) encoding the antibody are isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

An anti-α2 integrin antibody may be produced recombinantly, including as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. For prokaryotic host cells that do not recognize and process a eukaryotic signal sequence (e.g., an immunoglobulin signal sequence), the signal sequence is substituted by a prokaryotic signal sequence including, for example, pectate lyase (such as pelB), alkaline phosphatase, penicillinase, Ipp, or heat-stable enterotoxin II leaders. For yeast secretion, a yeast signal sequence may be utilized, including, for example, the yeast invertase leader, a factor leader (including *Saccharomyces* and *Kluyveromyces* α-factor leaders), or acid phosphatase leader, the *C. albicans* glucoamylase leader, or the signal described in WO90/13646. In mammalian cell expression, mammalian signal sequences as well as viral secretory leaders, for example, the herpes simplex gD signal, are available and may be utilized. The DNA for such a precursor region (e.g., the signal sequence) is ligated in reading frame to DNA encoding an anti-α2 integrin antibody.

Both expression and cloning vectors contain a nucleic acid sequence that enables the vector to replicate in one or more selected host cells. Generally, in cloning vectors, this sequence is one that enables the vector to replicate independently of the host chromosomal DNA, and includes origins of replication or autonomously replicating sequences. Such sequences are well known for a variety of bacteria, yeast, and viruses. For example, the origin of replication from the plasmid pBR322 is suitable for most gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (e.g., the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, (e.g., the gene encoding D-alanine racemase for Bacilli).

One example of a selection scheme utilizes a drug to arrest growth of a host cell. Those cells that are successfully transformed with a heterologous gene produce a protein conferring drug resistance and thus survive the selection regimen. Examples of such dominant selection use the drugs methotrexate, neomycin, histidinol, puromycin, mycophenolic acid and hygromycin.

Another example of suitable selectable markers for mammalian cells are those that enable the identification of cells competent to take up the anti-α2 integrin antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding anti-α2 integrin antibody, wild-type DHFR protein, and another selectable marker such as aminoglycoside 3'-phosphotransferase (APH) can be selected by cell growth in medium containing a selection agent for the selectable marker, including an aminoglycosidic antibiotic, such as kanamycin, neomycin, or G418 (see e.g., U.S. Pat. No. 4,965,199).

One suitable selection gene for use in yeast is the trp1 gene present in the yeast plasmid YRp7 (Stinchcomb et al., Nature, 282: 39 (1979)). The trp1 gene provides a selection marker for a mutant strain of yeast lacking the ability to grow in tryptophan, for example, ATCC No. 44076 or PEP4-1 (see, e.g., Jones, Genetics, 85: 12 (1977)). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6µ circular plasmid pKD1 can be used for transformation of *Kluyveromyces* yeasts. Alternatively, an expression system for large-scale production of recombinant calf chymosin was reported for *K. lactis* by Van den Berg, Bio/Technology, 8:135 (1990). Stable multi-copy expression vectors for secretion of mature recombinant human serum albumin by industrial strains of *Kluyveromyces* have also been disclosed (see, e.g., Fleer et al., Bio/Technology, 9: 968-975 (1991)).

Expression and cloning vectors usually contain a promoter that is recognized by the host organism and is operably linked to the anti-α2 integrin antibody nucleic acid. Promoters suitable for use with prokaryotic hosts include the arabinose promoter (e.g., araB), phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-α2 integrin antibody.

Promoter sequences are known for eukaryotes. Most eukaryotic genes have an AT-rich region located approximately 25 to 30 bases upstream from the site where transcription is, initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. Such sequences are suitably inserted into eukaryotic expression vectors.

Examples of suitable promoter sequences for use with yeast hosts include but are not limited to the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-α2 integrin antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus or Simian Virus 40 (SV40), from heterologous mammalian promoters, for example, the actin promoter or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446, and a modification of this system is described in U.S. Pat. No. 4,601,978 (see, also Reyes et al., Nature 297: 598-601 (1982) on expression of human β-interferon cDNA in mouse cells under the control of a thymidine kinase promoter from herpes simplex virus). Alternatively, the rous sarcoma virus long terminal repeat can be used as the promoter.

Transcription of DNA encoding an anti-α2 integrin antibody by higher eukaryotes is often increased by inserting an enhancer sequence into the vector. Many enhancer sequences are now known from mammalian genes (globin, elastase, albumin, α-fetoprotein, and insulin). Often, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers (see, also, e.g., Yaniv, Nature 297: 17-18 (1982) on enhancing elements for activation of eukaryotic promoters). The enhancer may be spliced into the vector at a position 5' or 3' to the anti-α2 integrin antibody-encoding sequence, but is preferably located at a site 5' from the promoter. Other gene regulation systems well known in the art (e.g. inducible systems, such as tetracycline inducible systems and GeneSwitch™) can be used to control the transcription of DNA encoding an anti-α2 integrin.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an anti-α2 integrin antibody. One useful transcription termination component is the bovine growth hormone polyadenylation region (see, e.g., WO94/11026 and the expression vector disclosed therein).

Suitable host cells for cloning or expressing the DNA in the vectors herein are the prokaryote, yeast, or higher eukaryote cells as described above. Suitable prokaryotes for this purpose include eubacteria, including gram-negative or gram-positive organisms, for example, Enterobacteriaceae such as Escherichia, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. Suitable *E. coli* cloning hosts include *E. coli* 294 (ATCC 31,446), *E. coli* B, *E. coli* X1776 (ATCC 31,537), and *E. coli* W3110 (ATCC 27,325).

In addition to prokaryotes, eukaryotic microbes such as filamentous fungi or yeast are suitable cloning or expression hosts for anti-alpha 2 integrin antibody-encoding vectors. *Saccharomyces cerevisiae*, or common baker's yeast, is the most commonly used among lower eukaryotic host microorganisms. However, a number of other genera, species, and Strains are commonly available and useful, such as *Schizosaccharomyces pombe; Kluyveromyces* hosts including *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, or *K. marxianus; yarrowia* (EP 402,226); *Pichia pastoris* (EP 183,070); *Candida; Trichoderma reesia* (EP 244, 234); *Neurospora crassa; Schwanniomyces* such as *Schwanniomyces occidentalis*; and filamentous fungi including *Neurospora, Penicillium, Tolypocladium*, or *Aspergillus* hosts such as *A. nidulans* or *A. niger*.

Suitable host cells for the expression of glycosylated anti-α2 integrin antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, for example, the L-1 variant of *Autographa californica* NPV and the Bm-5 strain of *Bombyx mori* NPV, and such viruses may be used, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells, including a variety of mammalian cells, has become routine procedure. Examples of useful mammalian host cells include: a monkey kidney CV1 line transformed by SV40 (e.g., COS-7, ATCC CRL 1651); a human embryonic kidney line 293 or 293 cells subcloned for growth in suspension culture (see e.g., Graham et al., J. Gen Virol. 36: 59 (1977)); baby hamster kidney cells (e.g., BHK, ATCC CCL 10); Chinese hamster ovary (CHO) cells, including CHO cells lacking DHFR (see, e.g., DHFR Urlaub et al., Proc. Natl. Acad. Sci. USA 77: 4216 (1980)); mouse sertoli cells ((e.g., TM4, Mather, Biol. Reprod. 23: 243-251 (1980)); monkey kidney cells (e.g., CV1 ATCC CCL 70); African green monkey kidney cells (e.g., VERO-76, ATCC CRL-1587); human cervical carcinoma cells (e.g., HELA, ATCC CCL 2); canine kidney cells (e.g., MDCK, ATCC CCL 34); buffalo rat liver cells (e.g., BRL 3A, ATCC CRL 1442); human lung cells (e.g., W138, ATCC CCL 75); human liver cells (e.g., Hep G2, HB 8065); mouse mammary tumor (e.g., MMT 060562, ATCC CCL51); TRI cells (see, e.g., Mather et al., Annals N.Y Acad. Sci. 383: 44-68 (1982)); MRC 5 cells; FS4 cells; or a human hepatoma line (e.g., Hep G2).

Host cells are transformed with an above-described expression or cloning vectors for anti-α2 integrin antibody production and cultured in conventional nutrient media modified as appropriate for inducing promoters, selecting transformants and/or amplifying the genes encoding the desired sequences.

The host cells used to produce an anti-α2 integrin antibody may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes at al., Anal. Biochem. 102: 255 (1980), U.S. Pat. Nos. 4,767,704; 4,657,866; 4,927,762; 4,560,655; or 5,122,469; WO90103430; WO 87/00195; or U.S. patent Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. Culture conditions, such as temperature, pH, and the like, are selected by those skilled in the art, including those culture conditions previously used with the host cell selected for expression.

Anti-α2 integrin antibodies can be purified from cells, including microbial or mammalian cells using, for example, protein A chromatography, ion exchange chromatography, hydrophobic interaction chromatography, gel electrophoresis, dialysis, and/or affinity chromatography. The suitability of protein A as an affinity ligand depends on the species and isotype of any immunoglobulin Fc domain that is present in the antibody. Protein A can be used to purify antibodies that are based on human γ1, γ2, or γ4 heavy chains (see, e.g., Lindmark et al., J. Immunol. Meth. 62:1-13 (1983)). Protein G is useful for mouse isotypes and for human γ3 (see, e.g., Guss et al, EMBO J. 5:1516-1517 (1986)). The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Where the antibody comprises a CH3 domain, the Bakerbond ABX™ (J. T. Baker, Phillipsburg, N.J.) is useful for purification. Protein purification can include one or more of the following techniques such as fractionation on an ion-exchange column, ethanol precipitation, Reverse Phase HPLC, chromatography on silica, chromatography on heparin SEPHAROSE™, chromatography on an anion or cation exchange resin (e.g., a polyaspartic acid column), chromatofocusing, SDS-PAGE, ammonium sulfate precipitation and/or hydrophobic interaction chromatography. For example, it may be useful following any purification step(s), to subject a mixture comprising the antibody of interest and contaminants to low pH hydrophobic interaction chromatography using an elution buffer at a pH between about 2.5-4.5, preferably performed at low salt concentrations (e.g., from about 0-0.25M salt).

Formulations of an anti-α2 integrin antibody, including those for therapeutic administration, are prepared for storage by mixing the antibody having the desired degree of purity with optional physiologically acceptable carriers, diluents, excipients or stabilizers (Remington's Pharmaceutical Sciences 16th edition, Osol, A. Ed. (1980)), in the form of lyophilized formulations or aqueous solutions. Acceptable carriers, diluents, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, or other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). For therapeutic uses the anti-α2 integrin antibody of the present invention may be formulated e.g. in phosphate buffered saline (PBS) containing 0.03% Tween-80™.

The antibody formulation may also contain more than one active compound for the particular indication being treated, preferably those with complementary activities that do not adversely affect each other. It may be desirable to use anti-α2 integrin antibody in addition to one or more agents currently used to prevent or treat the disorder in question. In addition, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles or nanocapsules) or in macroemulsions. Such techniques are disclosed, for example, in Remington's Pharmaceutical Sciences 16th edition, Osol, A. Ed. (1980).

Formulations to be used for in vivo administration are preferably sterile. This is readily accomplished, for example, by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Therapeutic Uses of Humanized Anti-α2 Integrin Antibodies

An anti-α2 integrin antibody may be used to treat various α2β1 integrin associated disorders as described herein. The anti-α2 integrin antibody is administered by any suitable means, including parenteral, subcutaneous, intraperitoneal, intrapulmonary, or intranasal. If desired for local immunosuppressive treatment, intralesional administration of the antibody (including perfusing or otherwise contacting the graft with the antibody before transplantation) is done. Parenteral administration includes intramuscular, intravenous, intraarterial, intraperitoneal, or subcutaneous administration. In addition, the anti-α2 integrin antibody is suitably administered by pulse infusion, for example, with declining doses of the antibody. Preferably the dosing is given by injections, most preferably intravenous or subcutaneous injections. This may depend in part on whether the administration is brief or chronic. More preferably the anti-α2 integrin antibodies or the compositions as described herein are administered in the methods of the present invention by intravenous infusion, intravenous bolus, subcutaneous administration, subcutaneous infusion or subcutaneous bolus, whereas intravenous infusion or intravenous bolus is most preferred. The term "intravenous infusion" refers to introduction of a drug into the vein of an animal or human patient over a period of time greater than approximately 5 minutes, preferably between approximately 30 to 90 minutes, although, according to the invention, intravenous infusion is alternatively administered for 10 hours or less. The term "intravenous bolus" or "intravenous push" refers to drug administration into a vein of an animal or human such that the body receives the drug in approximately 15 minutes or less, preferably 5 minutes or less. The term "subcutaneous administration" refers to introduction of a drug under the skin of an animal or human patient, preferable within a pocket between the skin and underlying tissue, by relatively slow, sustained delivery from a drug receptacle. The pocket may be created by pinching or drawing the skin up and away from underlying tissue. The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. The term "subcutaneous bolus" refers to drug administration beneath the skin of an animal or human patient, where bolus drug delivery is preferably less than approximately 15 minutes, more preferably less than 5 minutes, and most preferably less than 60 seconds. Administration is preferably within a pocket between the skin and underlying tissue; where the pocket is created, for example, —by pinching or drawing the skin up and away from underlying tissue. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen. Intermittent or periodic dosing is a dosing that is continuous for a certain period of time and is at regular intervals that are preferably separated more than by one day.

"Therapeutically effective amount" or "effective amount" which are used synonymously herein, refer to an amount of the anti-α2 integrin antibodies described herein effective to ameliorate or prevent the symptoms, or prolong the survival of the subject being treated. Determination of a therapeutically effective amount is well within the capabilities of those skilled in the art, especially in light of the detailed disclosure provided herein. The term "therapeutically effective amount" of the anti-α2 integrin antibodies described herein specifically refers to the amount needed to delay or inhibit cancer e.g. tumor growth.

For the prevention or treatment of an α2β1 integrin-associated disorder, the appropriate dosage of antibody will depend on the type of disease to be treated, as defined above, the severity and course of the disease, whether the anti-α2 integrin antibody is administered for preventive or therapeutic purposes, previous therapy, the patient's clinical history and response to the antibody, and the discretion of the attending physician. The antibody is suitably administered to the patient at one time or over a series of treatments.

The anti-α2 integrin antibodies can be thus administered to a subject, preferably to human, in the method of the present invention, at a therapeutically effective amount ranging from about 0.1. to about 100 mg/kg. Preferably, a therapeutically effective amount ranging from about 1 to about 20 mg/kg, more preferably a therapeutically effective amount ranging from about 3 to about 10 mg/kg is administered to a subject, preferably to human. A therapeutically effective amount of the humanized antibody or binding fragment thereof can be administered to the subject in one or more therapeutically effective doses.

For the prevention or treatment of an α2β1 integrin-associated disorder, the appropriate dosage of antibody will depend on the type of disease to be treated, as defined above, the severity and course of the disease, whether the anti-α2 integrin antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of an α2β1 integrin-associated disorder from about 0.1 mg/kg to about 100 mg/kg of antibody is an initial candidate dosage for administration to the subject, whether, for example, by one or more separate administrations, or by continuous infusion. A typical daily dosage to e.g. human might range from 0.1 mg/k to 20 mg/kg or more, depending on the factors mentioned above. For repeated administrations over several days or longer, depending on the condition, the treatment is sustained until a desired suppression of disease symptoms occurs. However, other dosage regimens may be useful e.g. a once every two weeks dosis regimen seems preferable. The progress of this therapy is readily monitored by those skilled in the art.

An anti-α2 integrin antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, results from pharmacological and toxicity studies and other factors known to medical practitioners. A therapeutically effective amount of the antibody to be administered is determined by consideration of such, and is the minimum amount necessary to prevent, ameliorate, or treat an α2β1 integrin-associated disorder. Such amount is preferably below the amount that is toxic to the host or renders the host significantly more susceptible to infections.

The anti-α2 integrin antibody need not be, but may be optionally formulated, co-administered or used as an adjunct therapy with one or more agents currently used to prevent or treat the disorder in question. For example, in rheumatoid arthritis, the antibody may be given in conjunction with a glucocorticosteroid, Remicaid® or any approved treatment for rheumatoid arthritis. For multiple sclerosis, the antibody may be given in conjunction with an interferonβ, Avonex, Copaxon, or other approved therapies for treatment of the signs and symptoms of multiple sclerosis. For transplants, the antibody may be administered concurrently with or separate from an immunosuppressive agent as defined above, such as cyclosporin A, to modulate the immunosuppressant effect. Alternatively, or in addition, α2β1 integrin antagonists may be administered to the mammal suffering from an α2β1 integrin-associated disorder. The effective amount of such other agents depends on the amount of anti-α2 integrin antibody present in the formulation, the type of disorder or treatment, and other factors discussed above. These are generally used in the same dosages and with administration routes as used hereinbefore or about from 1 to 99% of the heretofore employed dosages.

The following examples are offered by way of illustration and not by way of limitation. The disclosures of all citations in the specification are expressly incorporated herein by reference.

EXAMPLES

Example 1: Humanized Anti-Alpha2 Integrin Antibody Variants with Enhanced Complement-Mediated Effector Function The humanized anti-α2 integrin antibodies described therein represent a novel subgroup of anti-α2 (anti-VLA2) antibodies, which are characterized by an unexpected lack of in vivo bleeding complications and/or by a lack of platelet α2β1 integrin activation. The IgG4 antibodies disclosed in WO2007/056858, however, do not carry effector functions such as ADCC and/or CDC, which are desired under certain circumstances, e.g. for the treatment of α2β1 integrin-associated cancers, where this functionality can lead to increased efficacy of treatment. Thus, it would be desirable to develop anti-α2β1 integrin antibodies that would exhibit these effector functions to a high degree.

The four isotypes of human IgG differ from each other in the potencies of effector functions and other activities. In general, the rank order of potency is IgG1≥IgG3>>IgG4≥IgG2 for ADCC and IgG3≥IgG1>>IgG2=IgG4 for CDC (Niwa R. et al., J Immunol Methods 2005; 306:151-60). In this study, one anti-VLA-2 IgG4 antibody disclosed in WO2007/056858 (with heavy chain SEQ ID 57, and light chain SEQ ID NO: 56) was used to create a new subgroup of anti-VLA2 antibodies consisting of naturally occurring human antibody isotype variants IgG1, IgG2, and IgG3; engineered human IgG1 isotype variants, and chimeras of human IgG1 and human IgG3 isotype variants. All variants were created by mutagenesis techniques based on overlap PCR assembly methods.

To generate full antibody variants, each newly created heavy chain vector was transfected with the same anti-VLA-2 kappa light chain vector, carrying the anti-VLA-2 kappa light chain cDNA coding light chain sequence (SEQ ID NO: 56) and having identical expression regulating elements as the heavy chain vectors described below. Consequently, the heavy chain of a novel anti-VLA2 antibody variant defines a novel full antibody variant; therefore a heavy chain and the corresponding full antibody are designated by the same name.

Variants Based on Naturally Occurring Human Antibody Isotypes

To create naturally occurring isotype variants heavy chains, the cDNA of the anti-VLA-2 IgG4 antibody encoding the heavy chain hinge and constant domains of SEQ ID NO: 57 (Kabat residue 119 (corresponding to residue 121 in SEQ ID NO: 57) to its C-terminus) were replaced by the corresponding cDNA sequence encoding amino-acid for the hinge and constant domains of human IgG1 (NCBI GenBank accession no. J00228.1, sequence from residue 1 to its C-terminus), human IgG2 (NCBI GenBank accession no. J00230.1, sequence from residue 1 to its C-terminus), and human IgG3 (NCBI GenBank accession no. X03604.1, sequence from residue 2 to its C-terminus). These naturally occurring heavy chain variants subsequently define novel anti-VLA2 antibodies which are designated heavy chain anti-VLA2 IgG1 (SEQ ID NO: 44), heavy chain anti-VLA2 IgG2 (SEQ ID NO: 45), and heavy chain anti-VLA2 IgG3 (SEQ ID NO: 46) respectively.

Variants Based on Human IgG1/IgG3 Hinge-Fc Domains Shuffling

Human IgG3 antibodies have generally enhanced CDC compared to human IgG1 antibodies, this due in part because IgG3 Fc has higher C1q-binding affinity than IgG1 Fc (Schumaker V N et al., Biochemistry, 1976, 15:5175-81.). A shuffling strategy of the human IgG1 hinge and constant domains with the hinge and constant domains of the human IgG3 was undertaken to generate chimeras of anti-VLA-2 IgG4 with enhanced CDC.

Two chimeras were constructed. A first chimera based on the anti-VLA-2 IgG4 was engineered to fuse the CH1 and the hinge from human IgG1 to the Fc portion of human IgG3 and referred herein as heavy chain anti-VLA-2 IgG-1133 (SEQ ID NO: 47); while a second construct based on anti-VLA-2 IgG3 was engineered to substitute the hinge from human 19G3 with the hinge from human IgG1, this later chimera is referred herein as heavy chain anti-VLA-2 IgG-3133 (SEQ ID NO: 48).

To create the anti-VLA-2 lgG-1133 heavy chain cDNA coding sequence (SEQ ID NO: 47), the part of heavy chain cDNA for anti-VLA-2 lgG1 encoding the CH2 and CH3 constant domains (encoding Kabat residues 231 to its c-terminus) in the expression vector for the anti-VLA-2 lgG1 was replaced with the corresponding part of a human lgG3 heavy chain gene (NCBI GenBank accession no. X03604.1, residues 161 to 377). For the anti-VLA-2 lgG-3133 heavy chain cDNA coding sequence (SEQ ID NO: 48), the part of heavy chain cDNA for anti-VLA-2 lgG3 encoding the hinge region (ELKTPLGbTTHTCPRCPEPKSCDTPPPCPRC-PEPKSCDTPPPCPRCPEPKSCDTPPPCPRCP from NCBI GenBank accession no. X03604.1) (SEQ ID NO: 58) in the expression vector for anti-VLA-2 lgG3 heavy chain was replaced with the corresponding part (EPKSCDKTH-TCPPCP) (SEQ ID NO: 59) of a human lgG1 heavy chain gene (NCBI GenBank accession no. J00228.1).

Amino Acid Mutant Anti-VLA2 Antibodies with Enhanced CDC

A number of variants of the anti-VLA-2 IgG1 were designed with the goal of enhancing complement dependent cytotoxicity (CDC). In the same way that Fc interactions with Fcγ receptors mediates ADCC, Fc interactions with the complement component C1q mediates CDC. Although there is currently no 3D structure available for the Fc/C1q complex, several studies have mapped the binding site on human IgG for C1q to a region centred on residues D270, K322, P329 and P331 (Idusogie et al., J Immunol Methods 2000, 164:4178-4184). Amino acid modifications were designed in the D269-K334 region of the CH2 domain to explore variants that may mediate enhanced CDC for the anti-VLA-2 IgG1 antibody.

To create these variant cDNA coding sequences, a cDNA coding the anti-VLA-2 IgG1 heavy chain (SEQ ID NO: 44) cDNA was mutated to include the following substitutions: S324N (referred herein as anti-VLA-2 IgG1-S324N; SEQ ID NO: 49), E269D (referred herein as anti-VLA-2 IgG1-E269D; SEQ ID NO:50), and S298A (referred herein as anti-VLA-2 IgG1-S298A; SEQ ID NO: 51). Further variants were created by combing these point mutations in pairs: E269D, S298A were combined to generate a variant referred herein as anti-VLA-2 IgG1-E269D/S298A (SEQ ID NO: 52); another combination referred herein as anti-VLA-2 IgG1-E269D/S324N (SEQ ID NO: 53) consisted of E269D and S324N; a third combination referred herein as anti-VLA-2 IgG1-S298A/S324N (SEQ ID NO: 54) combined S298A and S324N mutations. Finally all three mutations were added to create a variant referred herein as anti-VLA-2 IgG1-E269D/S298A/S324N (SEQ ID NO: 55).

These variant coding DNA sequences were ligated in a vector that is based on a modified pREP4 (Invitrogen, Calif., USA) vector carrying CMV promoter and Bovine Growth Hormone poly-adenylation signal. In this expression-vector, secretion was driven by the murine VJ2C leader peptide.

Production of Anti-VLA2 Antibody Variants

For transient expression, equal quantities of each vector heavy chain (above) and anti-VLA-2 kappa light chain vector were co-transfected into suspension-adapted HEK-EBNA cells (ATCC-CRL-10852) using Polyethyleneimine (PEI). Typically, 100 ml of cells in suspension at a density of 0.8-1.2 million cells per ml is transfected with a DNA-PEI mixture containing 50 μg of expression vector encoding the variant heavy chain and 50 μg expression vector light chain. When recombinant expression vectors encoding each engineered chain genes are introduced into the host cells, the construct is produced by further culturing the cells for a period of 4 to 5 days to allow for secretion into the culture medium (EX-CELL 293, HEK293-serum-free medium, Sigma, Buchs, Switzerland), supplemented with 0.1% pluronic acid, 4 mM glutamine, and 0.25 μg/ml geneticin. The construct was then purified from cell-free supernatant using recombinant Streamline rProtein A media (GE Healthcare Europe GmbH, Glattbrugg, Switzerland), and used for further analysis.

The expression levels of some of these variants are listed in Table 1.

TABLE 1

Transient expression levels of anti-VLA2 antibody variants

| Antibody | Expression (mg/L) |
| --- | --- |
| anti-VLA-2 IgG1 | 30 |
| anti-VLA-2 IgG2 | 8 |
| anti-VLA-2 IgG3 | 1 |
| anti-VLA-2 IgG1-S324N | 10 |
| anti-VLA-2 IgG-1133 | 4 |
| anti-VLA-2 IgG-3133 | 1.4 |

Complement Mediated Toxicity on HT1080 Cells

A cell-based assay was used to measure the capacity of the variants to mediate CDC. Lysis was measured using release of lactate dehydrogenase (LDH) to monitor lysis of variant-opsonized HT1080 cells by baby rabbit complement (Harlan Laboratories, C-0099F, AN VENRAY, The Netherlands). Target cells (HT1080, ATTC® No. CCL-121) were washed 2 times with complete medium (RPMI-1640 medium (Chemie Brunschwig AG, PAA, Basel, Switzerland) supplemented with 10% fetal bovine serum (FBS, Chemie Brunschwig AG, PAA, Basel, Switzerland) and 1% Ultra-glutamine (Lonza, Verviers, Belgium)) by centrifugation and resuspension. Variant-antibodies were added at the final concentration of 1 µg/ml. Baby rabbit serum was diluted to 7.5% with complete medium and added to antibody-opsonized target cells. Plates were incubated for 3 hours at 37° C. Cell cytotoxicity was measured using the Cyto Tox 96 Non-Radioactive Cytotoxicity Assay kit (Promega, Madison, USA).

FIG. 1 shows typical results for this assay with data performed in triplicate±standard deviation. In this assay, little specific lysis due to IgG1 control (data point no. 12) or the parental anti-VLA-2 IgG4 antibody (data point no. 1) or the anti-VLA-2 IgG2 (data point no. 3) antibody is observed. While no to very low level of CDC are expected from the latter naturally occurring isotypes, it is rather surprising that the anti-VLA-2 IgG1 (data point no. 2) did not lead to any significant increase in CDC as it was anticipated that an IgG1 antibody isotype had superior CDC to the IgG4 and IgG2 isotypes. Only when the S324N mutation is present, CDC is increased by at least 6.4 fold for anti-VLA-2 IgG1-S324N (data point no. 7), 6.6 fold for anti-VLA-2 IgG1-S298A/S324N (data point no. 11), and 9 fold for anti-VLA-2 IgG1-E269D/S298A/S324N (data point no. 10). Complement-induced lysis was also greatly increased for antibody variants having components of human IgG3 antibody isotype constant region, CDC was at least increased 5.6 fold for anti-VLA-2 IgG-1133 (data point no. 5), and at least increased 8.6 fold for anti-VLA-2 IgG-3133 (data point no. 6). Best CDC increase was observed for the naturally occurring variant anti-VLA-2 IgG3 (data point no. 4) with an enhancement of at least 9.6 fold over the parental anti-VLA-2 IgG4 antibody. In conclusion, these results provide evidence that the S324N mutation in the context of the anti-VLA-2 IgG1 antibody is able to restore potent Complement-induced lysis, while the anti-VLA-2 IgG3 variant is the most potent of the anti-VLA2 antibody variants at eliciting CDC.

Example 2: Humanized Anti-Alpha2 Integrin Antibody Variants with Enhanced Antibody-Dependent Cellular Cytotoxicity (ADCC)

Anti-VLA2 antibody variants investigated in the study described in Example 1 were assessed for their ability to elicit ADCC.

ADCC activities of antibodies were measured by lactate dehydrogenase (LDH)-releasing assay using the CytoTox 96 Non-Radoactive Cytotoxicity Assay kit (Promega, Madison, USA). Human peripheral blood mononuclear cells (PBMC) were purified from citrated whole blood by standard Ficoll-paque separation, resuspended in complete medium (RPMI-1640 medium (Chemie Brunschwig AG, PAA, Basel, Switzerland) supplemented with 10% fetal bovine serum (FBS, Chemie Brunschwig AG, PAA, Basel, Switzerland), 2 mM ultraglutamine 1 (Lonza, Verviers, Belgium) and 1% penicillin/streptomycin (Chemie Brunschwig AG, PAA, Basel, Switzerland)), and 100 U/ml of human IL-2 (Sigma, Mo., USA)) and incubated overnight at 37° C. The following day, PBMC were collected by centrifugation, washed twice and resuspended in culture medium at a density of $8 \times 10^6$ cells/ml. The cell line HT1080 was used as target cells. HT1080 cells were washed twice and resuspended in complete medium at a density of $0.2 \times 10^6$ cells/ml. Fifty microliters of antibody diluted at 1.5 µg/ml, with a final concentration of 0.1 µg/ml (FIG. 2) or 0.01 µg/ml (FIG. 3) were mixed with 50 µl of target cells, and added to an equivalent volume of PBMC into a U-bottomed 96-well plate. A target to effector ratio of 1:40 was used throughout the experiments. After 4 hours incubation at 37° C., cells were centrifuged and 50 µl samples of cell-free supernatant were collected, transferred to a flat-bottomed 96-well plate, and assayed. Percentage of lysis was calculated as follows: (Sample release−Target spontaneous release−Effector spontaneous release)/(Maximum release−Target spontaneous release)*100; where Target spontaneous release is the fluorescence from wells which only contained target cells, Effector spontaneous release is the fluorescence from wells which only contained effector cells, and Maximum release is the fluorescence from wells containing target cells which have been treated with lysis buffer. Background percentage of lysis obtained in absence of antibody (Target+Effector cells) was subtracted from the percentage of lysis of sample; data shown are the mean cytotoxicity percentage±standard deviation of triplicate wells using PBMC isolated from one donor.

Figure 2:
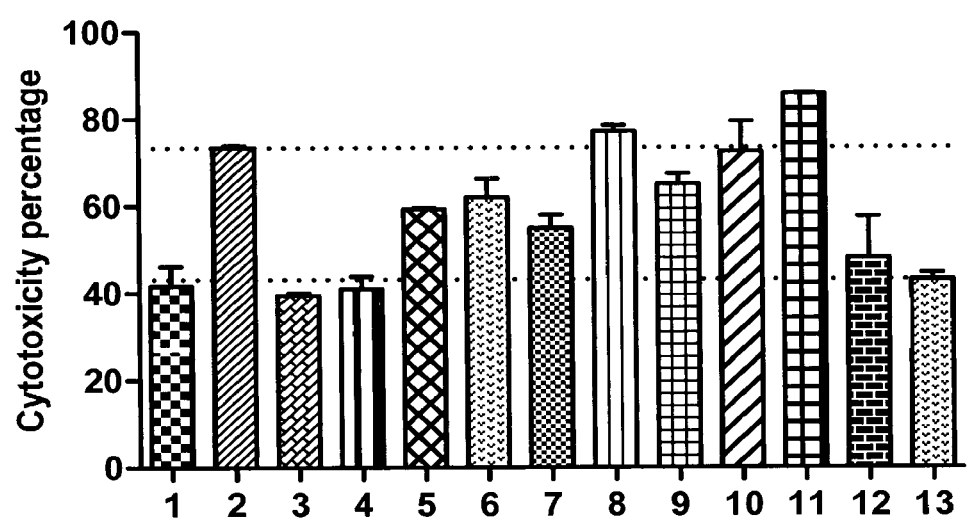
FIG. 2 shows cell-based ADCC assay of selected anti-VLA2 antibody variants at a final concentration of 0.1 μg/ml. (1) anti-VLA2 IgG4; (2) anti-VLA2 IgG1; (3) anti-VLA2 IgG2; (4) anti-VLA2 IgG3; (5) anti-VLA2 IgG1133; (6) anti-VLA2 IgG3133; (7) anti-VLA2 IgG1-S324N; (8) anti-VLA2 IgG1-S298A, (9) anti-VLA2 IgG1-E269D; (10) anti-VLA2 IgG1-E269D/S298A/S324N; (11) anti-VLA2 IgG1-S298A/S324N; (12) IgG1 control; (13) negative control—no antibody.

FIG. 2 show little specific ADCC due to IgG1 control antibody or the parental anti-VLA-2 IgG4 antibody (data point no. 1 and 12, respectively); data shown demonstrate that naturally occurring human IgG1 isotype of anti-VLA2 antibody has enhanced cellular cytotoxicity towards VLA-2+ expressing cells, and more preferably anti-VLA2-IgG1 antibody point mutants with the following rank order of potency: anti-VLA2-IgG1-S298A/S324N (data point no. 11; 2 fold increase)>anti-VLA2-IgG1-S298A (data point no. 8; 1.8 fold increase)>anti-VLA2-IgG1 (data point no. 2; 1.7 fold increase) or anti-VLA2-IgG1-E269D/S298A/S324N (data point no. 10; 1.7 fold increase)>anti-VLA2-IgG1-E269D (data point no. 9; 1.5 fold increase).

Figure 3:
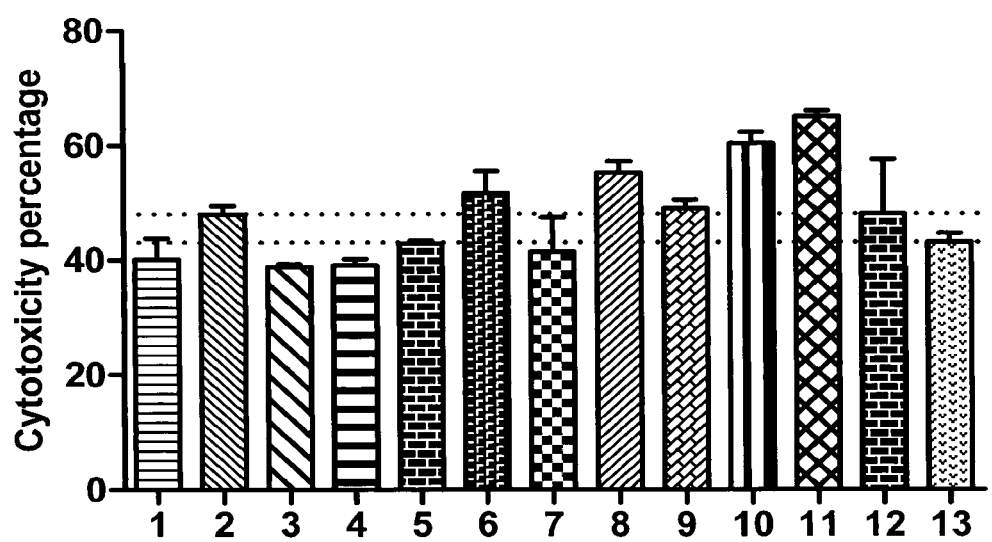
FIG. 3 shows cell-based ADCC assay of selected anti-VLA2 antibody variants at a final concentration of 0.01 μg/ml. (1) anti-VLA2 IgG4; (2) anti-VLA2 IgG1; (3) anti-VLA2 IgG2; (4) anti-VLA2 IgG3; (5) anti-VLA2 IgG1133; (6) anti-VLA2 IgG3133; (7) anti-VLA2 IgG1-S324N; (8) anti-VLA2 IgG1-S298A, (9) anti-VLA2 IgG1-E269D; (10) anti-VLA2 IgG1-E269D/S298A/S324N; (11) anti-VLA2 IgG1-S298A/S324N; (12) IgG1 control; (13) negative control—no antibody.

FIG. 3 show that a similar rank order of ADCC potency for the anti-VLA2 antibody variants is maintained at a ten-fold dilution of antibody.

The invention claimed is:

1. An antibody comprising a variant human IgG Fc region comprising amino acid substitution S298A that replaces serine at amino acid position 298 of a parent antibody with alanine, and amino acid substitution S324N replacing serine at amino acid position 324 of the parent antibody with asparagine, wherein the numbering of the amino acid positions is that of the EU index as in Kabat, wherein parent antibody is an antibody with a native human IgG1 heavy chain constant region, wherein variant IgG Fc region is identical to the native human IgG1 heavy chain constant region except for the S298A and S324N amino acid substitutions, and wherein the antibody exhibits improved CDC and ADCC as compared to the parent antibody.

2. The antibody of claim 1, wherein the variant $C_H$ comprises the amino acid sequence set forth as SEQ ID NO: 42.

3. A composition comprising the antibody of claim 1 and a pharmaceutically acceptable carrier.

4. A kit comprising the antibody of claim 1 and optional instructions.

5. The antibody of claim 1, wherein the antibody is selected from the group consisting of a chimeric antibody, a humanized antibody and a fully human antibody.

6. The antibody of claim 1, wherein the antibody is a humanized antibody.

7. The antibody of claim 1, wherein the antibody is a fully human antibody.

8. The antibody of claim 1, wherein the antibody is a anti-α2 integrin antibody.

9. The antibody of claim 8, comprising a light chain variable region sequence of any one of SEQ ID NOs:22-33, and a heavy chain variable region sequence of any one of SEQ ID NOs:8-19.

10. The antibody of claim 8, comprising a light chain variable region and a heavy chain variable region
wherein the light chain variable region comprises:
an LCDR1 comprising the amino acid sequence SAQSSVNYIH (SEQ ID NO:4);
an LCDR2 comprising the amino acid sequence DTSKLAS (SEQ ID NO:5); and
an LCDR3 comprising the amino acid sequence QQWTTNPLT (SEQ ID NO:6),
and wherein the heavy chain variable region comprises:
an HCDR1 comprising the amino acid sequence GFSLTNYGIH (SEQ ID NO:1);
an HCDR2 comprising the amino acid sequence VIWARGFTNYNSALMS (SEQ ID NO:2); and
an HCDR3 comprising the amino acid sequence ANDGVYYAMDY (SEQ ID NO:3).

* * * * *

SEQUENCE LISTING

```
<160> NUMBER OF SEQ ID NOS: 59

<210> SEQ ID NO 1
<211> LENGTH: 10
<212> TYPE: PRT
<213> ORGANISM: Artificial Sequence
<220> FEATURE:
<223> OTHER INFORMATION: HCDR1 [CDR1 of heavy chain variable region]

<400> SEQUENCE: 1

Gly Phe Ser Leu Thr Asn Tyr Gly Ile His
1               5                   10

<210> SEQ ID NO 2
<211> LENGTH: 16
<212> TYPE: PRT
<213> ORGANISM: Artificial Sequence
<220> FEATURE:
<223> OTHER INFORMATION: HCDR2 [CDR2 of heavy chain variable region]

<400> SEQUENCE: 2

Val Ile Trp Ala Arg Gly Phe Thr Asn Tyr Asn Ser Ala Leu Met Ser
1               5                   10                  15

<210> SEQ ID NO 3
<211> LENGTH: 11
<212> TYPE: PRT
<213> ORGANISM: Artificial Sequence
<220> FEATURE:
<223> OTHER INFORMATION: HCDR3 [CDR3 of heavy chain variable region]

<400> SEQUENCE: 3

Ala Asn Asp Gly Val Tyr Tyr Ala Met Asp Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: LCDR1 [CDR1 of light chain variable region]

<400> SEQUENCE: 4

Ser Ala Gln Ser Ser Val Asn Tyr Ile His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: LCDR2 [CDR2 of light chain variable region]

<400> SEQUENCE: 5

Asp Thr Ser Lys Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: LCDR3 [CDR3 of light chain variable region]

<400> SEQUENCE: 6

Gln Gln Trp Thr Thr Asn Pro Leu Thr
1               5
```

```
<210> SEQ ID NO 7
<211> LENGTH: 119
<212> TYPE: PRT
<213> ORGANISM: Artificial Sequence
<220> FEATURE:
<223> OTHER INFORMATION: humanized VH region
<220> FEATURE:
<221> NAME/KEY: VARIANT
<222> LOCATION: (30)..(30)
<223> OTHER INFORMATION: Xaa at position 30 can be Thr or Ile
<220> FEATURE:
<221> NAME/KEY: VARIANT
<222> LOCATION: (31)..(31)
<223> OTHER INFORMATION: Xaa at position 31 can be Asn or Ser
<220> FEATURE:
<221> NAME/KEY: VARIANT
<222> LOCATION: (37)..(37)
<223> OTHER INFORMATION: Xaa at position 37 can be Val or Ile
<220> FEATURE:
<221> NAME/KEY: VARIANT
<222> LOCATION: (48)..(48)
<223> OTHER INFORMATION: Xaa at position 48 can be Leu or Ile
<220> FEATURE:
<221> NAME/KEY: VARIANT
<222> LOCATION: (67)..(67)
<223> OTHER INFORMATION: Xaa at position 67 can be Val or Leu
<220> FEATURE:
<221> NAME/KEY: VARIANT
<222> LOCATION: (71)..(71)
<223> OTHER INFORMATION: Xaa at position 71 can be Lys or Val
<220> FEATURE:
<221> NAME/KEY: VARIANT
<222> LOCATION: (73)..(73)
<223> OTHER INFORMATION: Xaa at position 73 can be Asn or Thr
<220> FEATURE:
<221> NAME/KEY: VARIANT
<222> LOCATION: (78)..(78)
<223> OTHER INFORMATION: Xaa at position 78 can be Val or Phe
<220> FEATURE:
<221> NAME/KEY: VARIANT
<222> LOCATION: (94)..(94)
<223> OTHER INFORMATION: Xaa at position 94 can be Phe or Tyr

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Xaa Xaa Tyr
            20                  25                  30

Gly Ile His Trp Xaa Arg Gln Pro Pro Gly Lys Gly Leu Glu Trp Xaa
        35                  40                  45

Gly Val Ile Trp Ala Arg Gly Phe Thr Asn Tyr Asn Ser Ala Leu Met
    50                  55                  60

Ser Arg Xaa Thr Ile Ser Xaa Asp Xaa Ser Lys Asn Gln Xaa Ser Leu
65                  70                  75                  80

Lys Leu Ser Ser Val Thr Ala Ala Asp Thr Ala Val Tyr Xaa Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 8
<211> LENGTH: 119
<212> TYPE: PRT
<213> ORGANISM: Artificial Sequence
<220> FEATURE:
<223> OTHER INFORMATION: humanizedVH2.0
```

<400> SEQUENCE: 8

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115
```

<210> SEQ ID NO 9
<211> LENGTH: 119
<212> TYPE: PRT
<213> ORGANISM: Artificial Sequence
<220> FEATURE:
<223> OTHER INFORMATION: humanizedVH3.0

<400> SEQUENCE: 9

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115
```

<210> SEQ ID NO 10
<211> LENGTH: 119
<212> TYPE: PRT
<213> ORGANISM: Artificial Sequence
<220> FEATURE:
<223> OTHER INFORMATION: humanizedVH4.0

<400> SEQUENCE: 10

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Ile
        35                  40                  45
```

Gly Val Ile Trp Ala Arg Gly Phe Thr Asn Tyr Asn Ser Ala Leu Met
        50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 11
<211> LENGTH: 119
<212> TYPE: PRT
<213> ORGANISM: Artificial Sequence
<220> FEATURE:
<223> OTHER INFORMATION: humanizedVH5.0

<400> SEQUENCE: 11

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Ile
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 12
<211> LENGTH: 119
<212> TYPE: PRT
<213> ORGANISM: Artificial Sequence
<220> FEATURE:
<223> OTHER INFORMATION: humanizedVH6.0

<400> SEQUENCE: 12

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Ile
        35                  40                  45

Gly Val Ile Trp Ala Arg Gly Phe Thr Asn Tyr Asn Ser Ala Leu Met
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

```
Thr Leu Val Thr Val Ser Ser
        115

<210> SEQ ID NO 13
<211> LENGTH: 119
<212> TYPE: PRT
<213> ORGANISM: Artificial Sequence
<220> FEATURE:
<223> OTHER INFORMATION: humanizedVH7.0

<400> SEQUENCE: 13

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 14
<211> LENGTH: 119
<212> TYPE: PRT
<213> ORGANISM: Artificial Sequence
<220> FEATURE:
<223> OTHER INFORMATION: humanizedVH9.0
<220> FEATURE:
<221> NAME/KEY: misc_feature
<222> LOCATION: (48)..(48)
<223> OTHER INFORMATION: Xaa can be Leucine or Isoleucine

<400> SEQUENCE: 14

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Xaa
        35                  40                  45

Gly Val Ile Trp Ala Arg Gly Phe Thr Asn Tyr Asn Ser Ala Leu Met
    50                  55                  60

Ser Arg Leu Thr Ile Ser Val Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 15
<211> LENGTH: 119
```

```
<212> TYPE: PRT
<213> ORGANISM: Artificial Sequence
<220> FEATURE:
<223> OTHER INFORMATION: humanizedVH10.0

<400> SEQUENCE: 15

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Thr Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 16
<211> LENGTH: 119
<212> TYPE: PRT
<213> ORGANISM: Artificial Sequence
<220> FEATURE:
<223> OTHER INFORMATION: humanizedVH11.0
<220> FEATURE:
<221> NAME/KEY: misc_feature
<222> LOCATION: (48)..(48)
<223> OTHER INFORMATION: Xaa can be Leucine or Isoleucine

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Xaa
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Phe Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 17
<211> LENGTH: 119
<212> TYPE: PRT
<213> ORGANISM: Artificial Sequence
<220> FEATURE:
<223> OTHER INFORMATION: humanizedVH12.0
<220> FEATURE:
<221> NAME/KEY: misc_feature
<222> LOCATION: (48)..(48)
```

<223> OTHER INFORMATION: Xaa can be Leucine or Isoleucine

<400> SEQUENCE: 17

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Xaa
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 18
<211> LENGTH: 119
<212> TYPE: PRT
<213> ORGANISM: Artificial Sequence
<220> FEATURE:
<223> OTHER INFORMATION: humanizedVH13.0

<400> SEQUENCE: 18

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Ile
        35                  40                  45

Gly Val Ile Trp Ala Arg Gly Phe Thr Asn Tyr Asn Ser Ala Leu Met
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 19
<211> LENGTH: 119
<212> TYPE: PRT
<213> ORGANISM: Artificial Sequence
<220> FEATURE:
<223> OTHER INFORMATION: humanizedVH14.0
<220> FEATURE:
<221> NAME/KEY: misc_feature
<222> LOCATION: (48)..(48)
<223> OTHER INFORMATION: Xaa can be Leucine or Isoleucine

<400> SEQUENCE: 19

Gln Val Gln Leu Gln Glu Ser Gly Pro Gly Leu Val Lys Pro Ser Glu
1               5                   10                  15

```
Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Xaa
        35                  40                  45

Gly Val Ile Trp Ala Arg Gly Phe Thr Asn Tyr Asn Ser Ala Leu Met
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide: FW4 4-59
<220> FEATURE:
<221> NAME/KEY: misc_feature
<223> OTHER INFORMATION: NCBI entry, gi/33583/emb/CAA48104.1

<400> SEQUENCE: 20

Trp Gly Gln Gly Thr Leu Val Thr Val Ser Ser
1               5                   10

<210> SEQ ID NO 21
<211> LENGTH: 106
<212> TYPE: PRT
<213> ORGANISM: Artificial Sequence
<220> FEATURE:
<223> OTHER INFORMATION: humanized VL region
<220> FEATURE:
<221> NAME/KEY: VARIANT
<222> LOCATION: (1)..(1)
<223> OTHER INFORMATION: Xaa at position 1 can be Gln or Asp
<220> FEATURE:
<221> NAME/KEY: VARIANT
<222> LOCATION: (2)..(2)
<223> OTHER INFORMATION: Xaa at position 2 can be Phe or Val
<220> FEATURE:
<221> NAME/KEY: VARIANT
<222> LOCATION: (4)..(4)
<223> OTHER INFORMATION: Xaa at position 4 can be Leu or Met
<220> FEATURE:
<221> NAME/KEY: VARIANT
<222> LOCATION: (45)..(45)
<223> OTHER INFORMATION: Xaa at position 45 can be Lys or Leu
<220> FEATURE:
<221> NAME/KEY: VARIANT
<222> LOCATION: (46)..(46)
<223> OTHER INFORMATION: Xaa at position 46 can be Trp or Leu
<220> FEATURE:
<221> NAME/KEY: VARIANT
<222> LOCATION: (48)..(48)
<223> OTHER INFORMATION: Xaa at position 48 can be Tyr or Lys
<220> FEATURE:
<221> NAME/KEY: VARIANT
<222> LOCATION: (70)..(70)
<223> OTHER INFORMATION: Xaa at position 70 can be Tyr or Phe

<400> SEQUENCE: 21

Xaa Xaa Val Xaa Thr Gln Ser Pro Ala Phe Leu Ser Val Thr Pro Gly
1               5                   10                  15

Glu Lys Val Thr Ile Thr Cys Ser Ala Gln Ser Ser Val Asn Tyr Ile
```

```
                20                  25                  30

His Trp Tyr Gln Gln Lys Pro Asp Gln Ala Pro Lys Xaa Xaa Ile Xaa
            35                  40                  45

Asp Thr Ser Lys Leu Ala Ser Gly Val Pro Ser Arg Phe Ser Gly Ser
        50                  55                  60

Gly Ser Gly Thr Asp Xaa Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 22
<211> LENGTH: 106
<212> TYPE: PRT
<213> ORGANISM: Artificial Sequence
<220> FEATURE:
<223> OTHER INFORMATION: humanizedVL2.0Q

<400> SEQUENCE: 22

Gln Phe Val Leu Thr Gln Ser Pro Ala Phe Leu Ser Val Thr Pro Gly
1               5                   10                  15

Glu Lys Val Thr Ile Thr Cys Ser Ala Gln Ser Ser Val Asn Tyr Ile
            20                  25                  30

His Trp Tyr Gln Gln Lys Pro Asp Gln Ala Pro Lys Lys Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 23
<211> LENGTH: 106
<212> TYPE: PRT
<213> ORGANISM: Artificial Sequence
<220> FEATURE:
<223> OTHER INFORMATION: humanizedVL3.0Q

<400> SEQUENCE: 23

Gln Phe Val Leu Thr Gln Ser Pro Ala Phe Leu Ser Val Thr Pro Gly
1               5                   10                  15

Glu Lys Val Thr Ile Thr Cys Ser Ala Gln Ser Ser Val Asn Tyr Ile
            20                  25                  30

His Trp Tyr Gln Gln Lys Pro Asp Gln Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105
```

<210> SEQ ID NO 24
<211> LENGTH: 106
<212> TYPE: PRT
<213> ORGANISM: Artificial Sequence
<220> FEATURE:
<223> OTHER INFORMATION: humanizedVL4.0Q

<400> SEQUENCE: 24

```
Asp Val Val Met Thr Gln Ser Pro Ala Phe Leu Ser Val Thr Pro Gly
1               5                   10                  15

Glu Lys Val Thr Ile Thr Cys Ser Ala Gln Ser Ser Val Asn Tyr Ile
            20                  25                  30

His Trp Tyr Gln Gln Lys Pro Asp Gln Ala Pro Lys Lys Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105
```

<210> SEQ ID NO 25
<211> LENGTH: 106
<212> TYPE: PRT
<213> ORGANISM: Artificial Sequence
<220> FEATURE:
<223> OTHER INFORMATION: humanizedVL5.0Q

<400> SEQUENCE: 25

```
Asp Phe Val Leu Thr Gln Ser Pro Ala Phe Leu Ser Val Thr Pro Gly
1               5                   10                  15

Glu Lys Val Thr Ile Thr Cys Ser Ala Gln Ser Ser Val Asn Tyr Ile
            20                  25                  30

His Trp Tyr Gln Gln Lys Pro Asp Gln Ala Pro Lys Lys Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105
```

<210> SEQ ID NO 26
<211> LENGTH: 106
<212> TYPE: PRT
<213> ORGANISM: Artificial Sequence
<220> FEATURE:
<223> OTHER INFORMATION: humanizedVL6.0Q

<400> SEQUENCE: 26

```
Gln Phe Val Met Thr Gln Ser Pro Ala Phe Leu Ser Val Thr Pro Gly
1               5                   10                  15

Glu Lys Val Thr Ile Thr Cys Ser Ala Gln Ser Ser Val Asn Tyr Ile
            20                  25                  30

His Trp Tyr Gln Gln Lys Pro Asp Gln Ala Pro Lys Lys Trp Ile Tyr
```

```
                35                  40                  45
Asp Thr Ser Lys Leu Ala Ser Gly Val Pro Ser Arg Phe Ser Gly Ser
            50                  55                  60
Gly Ser Gly Thr Asp Tyr Thr Phe Thr Ile Ser Ser Leu Glu Ala Glu
 65                 70                  75                  80
Asp Ala Ala Thr Tyr Tyr Cys Gln Gln Trp Thr Thr Asn Pro Leu Thr
                85                  90                  95
Phe Gly Gln Gly Thr Lys Val Glu Ile Lys
                100                 105

<210> SEQ ID NO 27
<211> LENGTH: 106
<212> TYPE: PRT
<213> ORGANISM: Artificial Sequence
<220> FEATURE:
<223> OTHER INFORMATION: humanizedVL7.0Q

<400> SEQUENCE: 27

Asp Phe Val Met Thr Gln Ser Pro Ala Phe Leu Ser Val Thr Pro Gly
 1               5                  10                  15
Glu Lys Val Thr Ile Thr Cys Ser Ala Gln Ser Ser Val Asn Tyr Ile
                20                  25                  30
His Trp Tyr Gln Gln Lys Pro Asp Gln Ala Pro Lys Lys Trp Ile Tyr
                35                  40                  45
Asp Thr Ser Lys Leu Ala Ser Gly Val Pro Ser Arg Phe Ser Gly Ser
            50                  55                  60
Gly Ser Gly Thr Asp Tyr Thr Phe Thr Ile Ser Ser Leu Glu Ala Glu
 65                 70                  75                  80
Asp Ala Ala Thr Tyr Tyr Cys Gln Gln Trp Thr Thr Asn Pro Leu Thr
                85                  90                  95
Phe Gly Gln Gly Thr Lys Val Glu Ile Lys
                100                 105

<210> SEQ ID NO 28
<211> LENGTH: 106
<212> TYPE: PRT
<213> ORGANISM: Artificial Sequence
<220> FEATURE:
<223> OTHER INFORMATION: humanizedVL8.0Q

<400> SEQUENCE: 28

Gln Phe Val Leu Thr Gln Ser Pro Ala Phe Leu Ser Val Thr Pro Gly
 1               5                  10                  15
Glu Lys Val Thr Ile Thr Cys Ser Ala Gln Ser Ser Val Asn Tyr Ile
                20                  25                  30
His Trp Tyr Gln Gln Lys Pro Asp Gln Ala Pro Lys Lys Trp Ile Tyr
                35                  40                  45
Asp Thr Ser Lys Leu Ala Ser Gly Val Pro Ser Arg Phe Ser Gly Ser
            50                  55                  60
Gly Ser Gly Thr Asp Phe Thr Phe Thr Ile Ser Ser Leu Glu Ala Glu
 65                 70                  75                  80
Asp Ala Ala Thr Tyr Tyr Cys Gln Gln Trp Thr Thr Asn Pro Leu Thr
                85                  90                  95
Phe Gly Gln Gly Thr Lys Val Glu Ile Lys
                100                 105

<210> SEQ ID NO 29
<211> LENGTH: 106
```

```
<212> TYPE: PRT
<213> ORGANISM: Artificial Sequence
<220> FEATURE:
<223> OTHER INFORMATION: humanizedVL9.0Q

<400> SEQUENCE: 29

Gln Phe Val Leu Thr Gln Ser Pro Ala Phe Leu Ser Val Thr Pro Gly
1               5                   10                  15

Glu Lys Val Thr Ile Thr Cys Ser Ala Gln Ser Ser Val Asn Tyr Ile
            20                  25                  30

His Trp Tyr Gln Gln Lys Pro Asp Gln Ala Pro Lys Lys Trp Ile Lys
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 30
<211> LENGTH: 106
<212> TYPE: PRT
<213> ORGANISM: Artificial Sequence
<220> FEATURE:
<223> OTHER INFORMATION: humanizedVL10.0Q

<400> SEQUENCE: 30

Asp Phe Val Met Thr Gln Ser Pro Ala Phe Leu Ser Val Thr Pro Gly
1               5                   10                  15

Glu Lys Val Thr Ile Thr Cys Ser Ala Gln Ser Ser Val Asn Tyr Ile
            20                  25                  30

His Trp Tyr Gln Gln Lys Pro Asp Gln Ala Pro Lys Lys Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 31
<211> LENGTH: 106
<212> TYPE: PRT
<213> ORGANISM: Artificial Sequence
<220> FEATURE:
<223> OTHER INFORMATION: humanizedVL11.0Q

<400> SEQUENCE: 31

Asp Phe Val Met Thr Gln Ser Pro Ala Phe Leu Ser Val Thr Pro Gly
1               5                   10                  15

Glu Lys Val Thr Ile Thr Cys Ser Ala Gln Ser Ser Val Asn Tyr Ile
            20                  25                  30

His Trp Tyr Gln Gln Lys Pro Asp Gln Ala Pro Lys Lys Trp Ile Tyr
        35                  40                  45

Asp Thr Ser Lys Leu Ala Ser Gly Val Pro Ser Arg Phe Ser Gly Ser
```

```
                50                  55                  60
Gly Ser Gly Thr Asp Phe Thr Phe Thr Ile Ser Ser Leu Glu Ala Glu
 65                  70                  75                  80

Asp Ala Ala Thr Tyr Tyr Cys Gln Gln Trp Thr Thr Asn Pro Leu Thr
                 85                  90                  95

Phe Gly Gln Gly Thr Lys Val Glu Ile Lys
            100                 105

<210> SEQ ID NO 32
<211> LENGTH: 106
<212> TYPE: PRT
<213> ORGANISM: Artificial Sequence
<220> FEATURE:
<223> OTHER INFORMATION: humanizedVL1.0Q

<400> SEQUENCE: 32

Gln Phe Val Leu Thr Gln Ser Pro Ala Phe Leu Ser Val Thr Pro Gly
 1               5                  10                  15

Glu Lys Val Thr Ile Thr Cys Ser Ala Gln Ser Ser Val Asn Tyr Ile
                 20                  25                  30

His Trp Tyr Gln Gln Lys Pro Asp Gln Ala Pro Lys Lys Trp Ile Tyr
             35                  40                  45

Asp Thr Ser Lys Leu Ala Ser Gly Val Pro Ser Arg Phe Ser Gly Ser
         50                  55                  60

Gly Ser Gly Thr Asp Tyr Thr Phe Thr Ile Ser Ser Leu Glu Ala Glu
 65                  70                  75                  80

Asp Ala Ala Thr Tyr Tyr Cys Gln Gln Trp Thr Thr Asn Pro Leu Thr
                 85                  90                  95

Phe Gly Gln Gly Thr Lys Val Glu Ile Lys
            100                 105

<210> SEQ ID NO 33
<211> LENGTH: 106
<212> TYPE: PRT
<213> ORGANISM: Artificial Sequence
<220> FEATURE:
<223> OTHER INFORMATION: humanizedVL12.0Q

<400> SEQUENCE: 33

Asp Phe Val Met Thr Gln Ser Pro Ala Phe Leu Ser Val Thr Pro Gly
 1               5                  10                  15

Glu Lys Val Thr Ile Thr Cys Ser Ala Gln Ser Ser Val Asn Tyr Ile
                 20                  25                  30

His Trp Tyr Gln Gln Lys Pro Asp Gln Ala Pro Lys Lys Leu Ile Tyr
             35                  40                  45

Asp Thr Ser Lys Leu Ala Ser Gly Val Pro Ser Arg Phe Ser Gly Ser
         50                  55                  60

Gly Ser Gly Thr Asp Phe Thr Phe Thr Ile Ser Ser Leu Glu Ala Glu
 65                  70                  75                  80

Asp Ala Ala Thr Tyr Tyr Cys Gln Gln Trp Thr Thr Asn Pro Leu Thr
                 85                  90                  95

Phe Gly Gln Gly Thr Lys Val Glu Ile Lys
            100                 105

<210> SEQ ID NO 34
<211> LENGTH: 10
<212> TYPE: PRT
<213> ORGANISM: Artificial Sequence
<220> FEATURE:
```

<223> OTHER INFORMATION: FW 4 of mature kappa light chain

<400> SEQUENCE: 34

Phe Gly Gln Gly Thr Lys Val Glu Ile Lys
1               5                   10

<210> SEQ ID NO 35
<211> LENGTH: 330
<212> TYPE: PRT
<213> ORGANISM: Artificial Sequence
<220> FEATURE:
<223> OTHER INFORMATION: variant human IgG 1133 heavy chain constant region

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Tyr Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Ile Phe Ser Cys Ser Val Met His Glu Ala Leu His Asn Arg Phe Thr
305                 310                 315                 320

Gln Lys Ser Leu Ser Leu Ser Pro Gly Lys

```
            325                 330

<210> SEQ ID NO 36
<211> LENGTH: 330
<212> TYPE: PRT
<213> ORGANISM: Artificial Sequence
<220> FEATURE:
<223> OTHER INFORMATION: variant human IgG 3133 heavy chain constant
      region

<400> SEQUENCE: 36

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Tyr Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Ile Phe Ser Cys Ser Val Met His Glu Ala Leu His Asn Arg Phe Thr
305                 310                 315                 320

Gln Lys Ser Leu Ser Leu Ser Pro Gly Lys
                325                 330

<210> SEQ ID NO 37
<211> LENGTH: 330
```

```
<212> TYPE: PRT
<213> ORGANISM: Artificial Sequence
<220> FEATURE:
<223> OTHER INFORMATION: variant human IgG1 heavy chain constant region
      E269D

<400> SEQUENCE: 37

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Asp Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 38
<211> LENGTH: 330
<212> TYPE: PRT
<213> ORGANISM: Artificial Sequence
<220> FEATURE:
<223> OTHER INFORMATION: variant human IgG1 heavy chain constant region
      S298A
```

<400> SEQUENCE: 38

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ala Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 39
<211> LENGTH: 330
<212> TYPE: PRT
<213> ORGANISM: Artificial Sequence
<220> FEATURE:
<223> OTHER INFORMATION: variant human IgG1 heavy chain constant region S324N

<400> SEQUENCE: 39

```
Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Asn Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 40
<211> LENGTH: 330
<212> TYPE: PRT
<213> ORGANISM: Artificial Sequence
<220> FEATURE:
<223> OTHER INFORMATION: variant human IgG1 heavy chain constant region
      E269D/S298A

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
                35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ala Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 41
<211> LENGTH: 330
<212> TYPE: PRT
<213> ORGANISM: Artificial Sequence
<220> FEATURE:
<223> OTHER INFORMATION: variant human IgG1 heavy chain constant region
      E269D/S324N

<400> SEQUENCE: 41

Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Asp Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Asn Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 42
<211> LENGTH: 330
<212> TYPE: PRT
<213> ORGANISM: Artificial Sequence
<220> FEATURE:
<223> OTHER INFORMATION: variant human IgG1 heavy chain constant region
      S298A/S324N

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95
```

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ala Thr Tyr Arg Val Val Ser Val Leu Thr Val Leu
                180                 185                 190

His Gln Asp Trp Leu Asn Gly Lys Glu Tyr Lys Cys Lys Val Asn Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 43
<211> LENGTH: 330
<212> TYPE: PRT
<213> ORGANISM: Artificial Sequence
<220> FEATURE:
<223> OTHER INFORMATION: variant human IgG1 heavy chain constant region
      E269D/S298A/S324N

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro 115                 120                 125
Lys Pro Lys Asp Thr Leu Met Ile Ser Arg Thr Pro Glu Val Thr Cys
130                 135                 140

Val Val Val Asp Val Ser His Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ala Thr Tyr Arg Val Val Ser Val Leu Thr Val Leu
            180                 185                 190

His Gln Asp Trp Leu Asn Gly Lys Glu Tyr Lys Cys Lys Val Asn Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 44
<211> LENGTH: 449
<212> TYPE: PRT
<213> ORGANISM: Artificial Sequence
<220> FEATURE:
<223> OTHER INFORMATION: heavy chain anti-VLA2 IgG1

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
                20                  25                  30

Gly Ile His Trp Ile Arg Gln Pro Pro Gly Lys Gly Leu Glu Trp Leu
            35                  40                  45

Gly Val Ile Trp Ala Arg Gly Phe Thr Asn Tyr Asn Ser Ala Leu Met
        50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp

```
                145                 150                 155                 160
        Asn Ser Gly Ala Leu Thr Ser Gly Val His Thr Phe Pro Ala Val Leu
                        165                 170                 175

Gln Ser Ser Gly Leu Tyr Ser Leu Ser Ser Val Val Thr Val Pro Ser
                        180                 185                 190

Ser Ser Leu Gly Thr Gln Thr Tyr Ile Cys Asn Val Asn His Lys Pro
                        195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Gly Pro
        225                 230                 235                 240

Ser Val Phe Leu Phe Pro Pro Lys Pro Lys Asp Thr Leu Met Ile Ser
                        245                 250                 255

Arg Thr Pro Glu Val Thr Cys Val Val Val Asp Val Ser His Glu Asp
                        260                 265                 270

Pro Glu Val Lys Phe Asn Trp Tyr Val Asp Gly Val Glu Val His Asn
                        275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
        305                 310                 315                 320

Tyr Lys Cys Lys Val Ser Asn Lys Ala Leu Pro Ala Pro Ile Glu Lys
                        325                 330                 335

Thr Ile Ser Lys Ala Lys Gly Gln Pro Arg Glu Pro Gln Val Tyr Thr
                        340                 345                 350

Leu Pro Pro Ser Arg Asp Glu Leu Thr Lys Asn Gln Val Ser Leu Thr
                        355                 360                 365

Cys Leu Val Lys Gly Phe Tyr Pro Ser Asp Ile Ala Val Glu Trp Glu
                        370                 375                 380

Ser Asn Gly Gln Pro Glu Asn Asn Tyr Lys Thr Thr Pro Pro Val Leu
        385                 390                 395                 400

Asp Ser Asp Gly Ser Phe Phe Leu Tyr Ser Lys Leu Thr Val Asp Lys
                        405                 410                 415

Ser Arg Trp Gln Gln Gly Asn Val Phe Ser Cys Ser Val Met His Glu
                        420                 425                 430

Ala Leu His Asn His Tyr Thr Gln Lys Ser Leu Ser Leu Ser Pro Gly
                        435                 440                 445

Lys

<210> SEQ ID NO 45
<211> LENGTH: 445
<212> TYPE: PRT
<213> ORGANISM: Artificial Sequence
<220> FEATURE:
<223> OTHER INFORMATION: heavy chain anti-VLA2 IgG2

<400> SEQUENCE: 45

Gln Val Gln Leu Gln Glu Ser Gly Pro Gly Leu Val Lys Pro Ser Glu
        1               5                   10                  15

Thr Leu Ser Leu Thr Cys Thr Val Ser Gly Phe Ser Leu Thr Asn Tyr
                        20                  25                  30

Gly Ile His Trp Ile Arg Gln Pro Pro Gly Lys Gly Leu Glu Trp Leu
                        35                  40                  45

Gly Val Ile Trp Ala Arg Gly Phe Thr Asn Tyr Asn Ser Ala Leu Met
                50                  55                  60
```

```
Ser Arg Leu Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Ala Asn Asp Gly Val Tyr Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 46
<211> LENGTH: 496
<212> TYPE: PRT
<213> ORGANISM: Artificial Sequence
<220> FEATURE:
```

<223> OTHER INFORMATION: heavy chain anti-VLA2 IgG3

<400> SEQUENCE: 46

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asn His Lys Pro
        195                 200                 205

Ser Asn Thr Lys Val Asp Lys Arg Val Glu Leu Lys Thr Pro Leu Gly
    210                 215                 220

Asp Thr Thr His Thr Cys Pro Arg Cys Pro Glu Pro Lys Ser Cys Asp
225                 230                 235                 240

Thr Pro Pro Pro Cys Pro Arg Cys Pro Glu Pro Lys Ser Cys Asp Thr
                245                 250                 255

Pro Pro Pro Cys Pro Arg Cys Pro Glu Pro Lys Ser Cys Asp Thr Pro
            260                 265                 270

Pro Pro Cys Pro Arg Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Gln Phe Lys Trp Tyr Val Asp Gly Val Glu Val His Asn Ala
                325                 330                 335

Lys Thr Lys Pro Arg Glu Glu Gln Tyr Asn Ser Thr Phe Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380

Ile Ser Lys Thr Lys Gly Gln Pro Arg Glu Pro Gln Val Tyr Thr Leu
385                 390                 395                 400
```

```
Pro Pro Ser Arg Glu Glu Met Thr Lys Asn Gln Val Ser Leu Thr Cys
                405                 410                 415
Leu Val Lys Gly Phe Tyr Pro Ser Asp Ile Ala Val Glu Trp Glu Ser
            420                 425                 430
Ser Gly Gln Pro Glu Asn Asn Tyr Asn Thr Thr Pro Met Leu Asp
        435                 440                 445
Ser Asp Gly Ser Phe Phe Leu Tyr Ser Lys Leu Thr Val Asp Lys Ser
    450                 455                 460
Arg Trp Gln Gln Gly Asn Ile Phe Ser Cys Ser Val Met His Glu Ala
465                 470                 475                 480
Leu His Asn Arg Phe Thr Gln Lys Ser Leu Ser Leu Ser Pro Gly Lys
                485                 490                 495

<210> SEQ ID NO 47
<211> LENGTH: 449
<212> TYPE: PRT
<213> ORGANISM: Artificial Sequence
<220> FEATURE:
<223> OTHER INFORMATION: heavy chain anti-VLA2 IgG (1133)

<400> SEQUENCE: 47

Gln Val Gln Leu Gln Glu Ser Gly Pro Gly Leu Val Lys Pro Ser Glu
1               5                   10                  15
Thr Leu Ser Leu Thr Cys Thr Val Ser Gly Phe Ser Leu Thr Asn Tyr
            20                  25                  30
Gly Ile His Trp Ile Arg Gln Pro Pro Gly Lys Gly Leu Glu Trp Leu
        35                  40                  45
Gly Val Ile Trp Ala Arg Gly Phe Thr Asn Tyr Asn Ser Ala Leu Met
    50                  55                  60
Ser Arg Leu Thr Ile Ser Lys Asp Asn Ser Lys Asn Gln Val Ser Leu
65                  70                  75                  80
Lys Leu Ser Ser Val Thr Ala Ala Asp Thr Ala Val Tyr Tyr Cys Ala
                85                  90                  95
Arg Ala Asn Asp Gly Val Tyr Tyr Ala Met Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
```

```
Pro Glu Val Gln Phe Lys Trp Tyr Val Asp Gly Val Glu Val His Asn
            275                 280                 285

Ala Lys Thr Lys Pro Arg Glu Glu Gln Tyr Asn Ser Thr Phe Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Ser Gly Gln Pro Glu Asn Asn Tyr Asn Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Ile Phe Ser Cys Ser Val Met His Glu
            420                 425                 430

Ala Leu His Asn Arg Phe Thr Gln Lys Ser Leu Ser Leu Ser Pro Gly
        435                 440                 445

Lys

<210> SEQ ID NO 48
<211> LENGTH: 449
<212> TYPE: PRT
<213> ORGANISM: Artificial Sequence
<220> FEATURE:
<223> OTHER INFORMATION: heavy chain anti-VLA2 IgG (3133)

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
                180             185             190
Ser Ser Leu Gly Thr Gln Thr Tyr Thr Cys Asn Val Asn His Lys Pro
        195                 200                 205
Ser Asn Thr Lys Val Asp Lys Arg Val Glu Pro Lys Ser Cys Asp Lys
        210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Gln Phe Lys Trp Tyr Val Asp Gly Val Glu Val His Asn
            275                 280                 285
Ala Lys Thr Lys Pro Arg Glu Glu Gln Tyr Asn Ser Thr Phe Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Thr Lys Gly Gln Pro Arg Glu Pro Gln Val Tyr Thr
                340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
        370                 375                 380
Ser Ser Gly Gln Pro Glu Asn Asn Tyr Asn Thr Thr Pro Pro Met Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Ile Phe Ser Cys Ser Val Met His Glu
                420                 425                 430
Ala Leu His Asn Arg Phe Thr Gln Lys Ser Leu Ser Leu Ser Pro Gly
            435                 440                 445
Lys

<210> SEQ ID NO 49
<211> LENGTH: 449
<212> TYPE: PRT
<213> ORGANISM: Artificial Sequence
<220> FEATURE:
<223> OTHER INFORMATION: heavy chain anti-VLA2 IgG1 S324N

<400> SEQUENCE: 49

Gln Val Gln Leu Gln Glu Ser Gly Pro Gly Leu Val Lys Pro Ser Glu
1               5                   10                  15
Thr Leu Ser Leu Thr Cys Thr Val Ser Gly Phe Ser Leu Thr Asn Tyr
            20                  25                  30
Gly Ile His Trp Ile Arg Gln Pro Pro Gly Lys Gly Leu Glu Trp Leu
        35                  40                  45
Gly Val Ile Trp Ala Arg Gly Phe Thr Asn Tyr Asn Ser Ala Leu Met
    50                  55                  60
Ser Arg Leu Thr Ile Ser Lys Asp Asn Ser Asn Gln Val Ser Leu
65                  70                  75                  80
Lys Leu Ser Ser Val Thr Ala Ala Asp Thr Ala Val Tyr Tyr Cys Ala
                85                  90                  95
```

Arg Ala Asn Asp Gly Val Tyr Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Asn Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 50
<211> LENGTH: 449
<212> TYPE: PRT
<213> ORGANISM: Artificial Sequence
<220> FEATURE:
<223> OTHER INFORMATION: heavy chain anti-VLA2 IgG1 E269D

<400> SEQUENCE: 50

-continued

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

-continued

```
                420                 425                 430
Ala Leu His Asn His Tyr Thr Gln Lys Ser Leu Ser Leu Ser Pro Gly
            435                 440                 445
Lys

<210> SEQ ID NO 51
<211> LENGTH: 449
<212> TYPE: PRT
<213> ORGANISM: Artificial Sequence
<220> FEATURE:
<223> OTHER INFORMATION: heavy chain anti-VLA2 IgG1 S298A

<400> SEQUENCE: 51

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ala Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

```
Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 52
<211> LENGTH: 449
<212> TYPE: PRT
<213> ORGANISM: Artificial Sequence
<220> FEATURE:
<223> OTHER INFORMATION: heavy chain anti-VLA2 IgG1 E269D/S298A

<400> SEQUENCE: 52

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
                20                  25                  30

Gly Ile His Trp Ile Arg Gln Pro Pro Gly Lys Gly Leu Glu Trp Leu
            35                  40                  45

Gly Val Ile Trp Ala Arg Gly Phe Thr Asn Tyr Asn Ser Ala Leu Met
        50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ala Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 53
<211> LENGTH: 449
<212> TYPE: PRT
<213> ORGANISM: Artificial Sequence
<220> FEATURE:
<223> OTHER INFORMATION: heavy chain anti-VLA2 IgG1 E269D/S324N

<400> SEQUENCE: 53

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

```
                145                 150                 155                 160
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Asn Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 54
<211> LENGTH: 449
<212> TYPE: PRT
<213> ORGANISM: Artificial Sequence
<220> FEATURE:
<223> OTHER INFORMATION: heavy chain anti-VLA2 IgG1 S298A/S324N

<400> SEQUENCE: 54

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Leu
            35                  40                  45

Gly Val Ile Trp Ala Arg Gly Phe Thr Asn Tyr Asn Ser Ala Leu Met
            50                  55                  60
```

Ser Arg Leu Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Ala Asn Asp Gly Val Tyr Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ala Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Asn Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 55
<211> LENGTH: 449
<212> TYPE: PRT

<213> ORGANISM: Artificial Sequence
<220> FEATURE:
<223> OTHER INFORMATION: heavy chain anti-VLA2 IgG1 E269D/S298A/S324N

<400> SEQUENCE: 55

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Asp Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ala Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Asn Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
```

```
                385                 390                 395                 400
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 56
<211> LENGTH: 213
<212> TYPE: PRT
<213> ORGANISM: Artificial Sequence
<220> FEATURE:
<223> OTHER INFORMATION: light chain anti-VLA2 IgG4

<400> SEQUENCE: 56

Asp Phe Val Met Thr Gln Ser Pro Ala Phe Leu Ser Val Thr Pro Gly
1               5                   10                  15

Glu Lys Val Thr Ile Thr Cys Ser Ala Gln Ser Ser Val Asn Tyr Ile
                20                  25                  30

His Trp Tyr Gln Gln Lys Pro Asp Gln Ala Pro Lys Lys Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 57
<211> LENGTH: 446
<212> TYPE: PRT
<213> ORGANISM: Artificial Sequence
<220> FEATURE:
<223> OTHER INFORMATION: heavy chain anti-VLA2 IgG4

<400> SEQUENCE: 57

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
```

-continued

```
               20                  25                  30
Gly Ile His Trp Ile Arg Gln Pro Pro Gly Lys Gly Leu Glu Trp Leu
            35                  40                  45

Gly Val Ile Trp Ala Arg Gly Phe Thr Asn Tyr Asn Ser Ala Leu Met
        50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445
```

```
<210> SEQ ID NO 58
<211> LENGTH: 62
<212> TYPE: PRT
<213> ORGANISM: Artificial Sequence
<220> FEATURE:
<223> OTHER INFORMATION: Synthetic peptide: hinge region of anti-VLA-2
      IgG3

<400> SEQUENCE: 58

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 59
<211> LENGTH: 15
<212> TYPE: PRT
<213> ORGANISM: Artificial Sequence
<220> FEATURE:
<223> OTHER INFORMATION: Synthetic peptide: part of a human IgG1 heavy
      chain gene

<400> SEQUENCE: 59

Glu Pro Lys Ser Cys Asp Lys Thr His Thr Cys Pro Pro Cys Pro
1               5                   10                  15
```